US005532348A

United States Patent [19]

Huibregtse et al.

[11] Patent Number: 5,532,348
[45] Date of Patent: Jul. 2, 1996

[54] E6 ASSOCIATED PROTEIN AND METHODS OF USE THEREOF

[75] Inventors: Jon M. Huibregtse, Brighton, Mass.; Martin Scheffner, Walldorf, Germany; Peter M. Howley, Wellesley, Mass.

[73] Assignee: United States of America, Washington, D.C.

[21] Appl. No.: 100,692

[22] Filed: Jul. 30, 1993

[51] Int. Cl.⁶ ................................................ C07H 21/04
[52] U.S. Cl. ................................. 536/23.5; 435/235.1
[58] Field of Search ............................... 536/23.5; 435/5, 435/235.1

[56] References Cited

PUBLICATIONS

AA. Huibregtse, et al., "Cloning and Expression of the cDNA for E6–AP, a Protein That Mediates the Interaction of the Human Papillomavirus E6 Oncoprotein with p53" Mol. Cell. Biol. 13(2):775–84 (Feb. 1993).
AB. Huibregtse, et al., "Localization of the E6–AP Regions That Direct Human Papillomavirus E6 Binding, Assocation with p53, and Ubiquitination of Associated Proteins" Mol. Cell. Biol. 13(8): 4918–4927 (Aug. 1993).
Oren et al., "Post–Translational Regulation of the 54K Cellular Tumor Antigen in Normal and Transformed Cells", Mol. Cell. Biol., 1:101–110 (1981).
zur Hausen and Schneider, "The Role of Papillomaviruses in Human Anogential Cancer", in The Papovavirides, vol. 2, Plenum, New York, 1987.
Schlegel et al., "Quantitative keratinocyte assay detects two biological activities of human papillomavirus DNA and identifies viral types associated with cervical carcinoma", EMBO J., 7:3181–3187 (1988).
Watanabe et al., "Human Papillomavirus Type 16 Transformation of Primary Human Embryonic Fibroblasts Requires Expression of Open Reading Frames E6 and E7", J. Virol., 63:965–969 (1989).
Münger et al., "Complex formation of human papillomavirus E7 proteins with the retinoblastoma tumor suppressor gene product", EMBO J., 8:4099–4105 (1989).
Finlay et al., "The p53 proto–Oncogene Can Act as a Suppressor of Transformation", Cell, 57:1083–1093 (1989).
Eliyahu et al., "Wild–type p53 can inhibit oncogene–mediated focus formation", Proc. Natl. Acad. Sci. USA, 86:8763–8767 (1989).
Lane and Benchimol, "p53: Oncogene or Anti–oncogene?" Genes and Devel., 4:1–8 (1990).
Werness et al., "Association of Human Papillomarvirus Types 16 and 18 E6 Proteins with p53," Science, 248:76–79 (Apr. 6, 1990).
Vogelstein, "A Deadly Inheeritance," Nature, 348:681–682 (Dec., 1990).
Malkin et al., "Germ Line p53 Mutations in a Familial Syndrome of Breast Cancer, Sarcomas, and Other Neoplasms," Science, 250:1233–1238 (Nov. 30, 1990).
Srivastava et al., "Germ–line transmission of a mutated p53 gene in a cancer–prone family with Li–Fraumeni syndrome," Nature, 348:747–749 (Dec., 1990).

Diller et al., "p53 Functions as a Cell Cycle Control Protein in Osteosarcomas", Mol. Cell. Biol., 10:5772–5781 (1990).
Werness et al., "Association of Human Papillomavirus Types 16 and 18 E6 Proteins with p53", Science, 248:76–79 (Apr. 6, 1990).
Scheffner et al., "The E6 Oncoprotein Encoded by Human Papillomavirus Types 16 and 18 promotes the Degradation of p53", Cell, 63:1129–1136 (1990).
Baker et al., "Suppression of Human Colorectal Carcinoma Cell Growth by Wild–Type p53," Science, 249:912–915 (Aug. 24, 1990).
Huibregtse et al., "A Cellular Protein Mediates Association of p53 with the E6 Oncoprotein of Human Papillomavirus Types 16 or 18", EMBO J., 10:4129–4135 (1991).
Wrede et al., "Expression of RB and p53 Proteins in HPV–Positive and HPV–Negative Cervical Carcinoma Cell Lines", Mol. Carcin., 4:171–175 (1991).
Scheffner et al., "The state of the p53 and retinoblastoma genes in human cervical carcinoma cell lines", Proc. Natl. Acad. Sci. USA, 88:5523–5527 (1991).
Martinez et al., "Cellular localization and cell cycle regulation by a temperature–sensitive p53 protein", Genes and Devel., 5:151–159 (1991).
Levine et al., "The p53 tumour suppressor gene," Nature, 351:453–456 (Jun. 6, 1991).
Ginsberg et al., "Wild–type p53 can down–modulate the activity of various promoters", Proc. Natl. Acad. Sci. USA, 88:9979–9983 (1991).
Fakharzadeh et al., "Tumorigenic potential associated with enhanced expression of a gene that is amplified in a mouse tumor cell line", EMBO J., 10:1565–1569 (1991).
Oliner et al., "Amplification of a Gene Encoding a p53–associated Protein in Human Sarcomas", Nature, 358:80–83 (Jul. 2, 1992).
Momand et al., "The mdm–2 Oncogene Product Forms a Complex with the p53 Protein and Inhibits p53–Mediated Transactivation", Cell, 69:1237–1245 (1992).
Kern et al., "Oncogenic Forms of p53 Inhibit p53–Regulated Gene Expression," Science, 256:827–830 (May 8, 1992).
Farmer et al., "Wild–type p53 activates transcription in vitro," Nature, 358:83–86 (Jul. 2, 1992).
Huibregtse et al., Mol. Cell. Biol. 13(2):775–784, Feb. 1983.
Prives et al., Genes Dev., 7(4):529–534, Apr. 1993.

Primary Examiner—W. Gary Jones
Assistant Examiner—Scott W. Houtteman
Attorney, Agent, or Firm—Townsend and Townsend and Crew

[57] ABSTRACT

The present invention provides compositions of isolated and purified E6 Associated Protein and fragments thereof. Also provided are nucleic acid constructs encoding E6 Associated Protein. These compositions may be employed to identify compounds which inhibit binding of high risk HPV E6 to p53. The compositions of the present invention may also be used in methods to detect the presence of high risk HPV in biological samples.

5 Claims, 12 Drawing Sheets

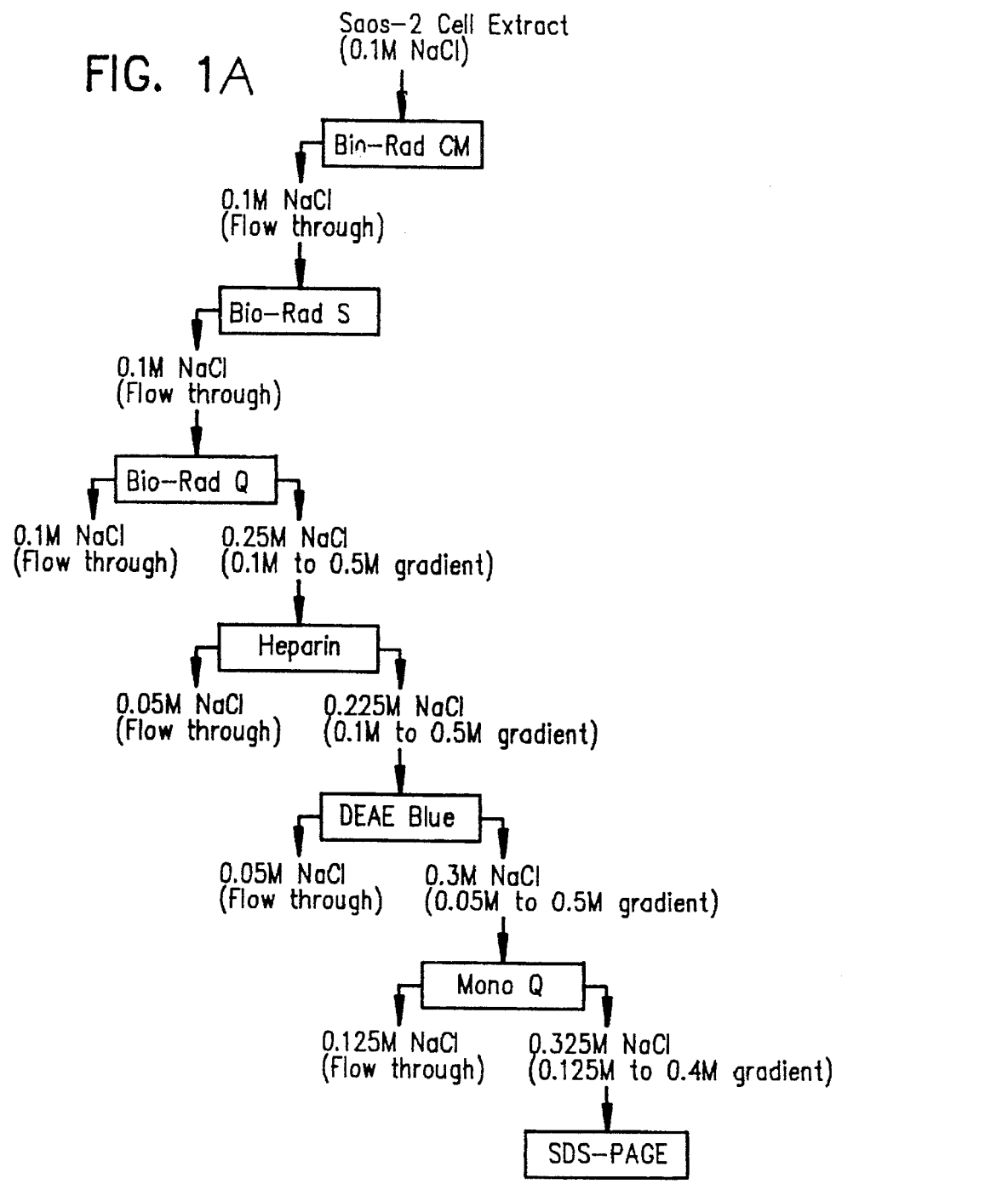
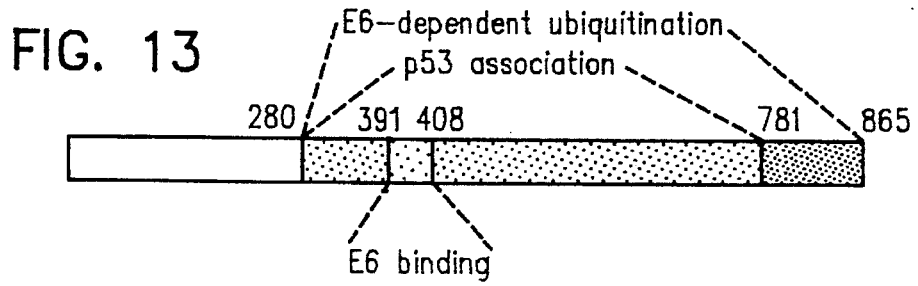

FIG. 10A
| | | E6-AP amino acids: |
|---|---|---|
| N1-C1 | | 37-865 |
| N2-C1 | | 213-865 |
| N3-C1 | | 248-865 |
| N4-C1 | | 280-865 |
| N5-C1 | | 322-865 |
| N6-C1 | | 371-865 |
| N1-C2 | | 37-831 |
| N1-C3 | | 37-781 |
| N1-C4 | | 37-729 |
| N1-C5 | | 37-678 |
| N1-C1 Δ391-408 | | 37-865 Δ391-408 |
FIG. 10B
FIG. 10C
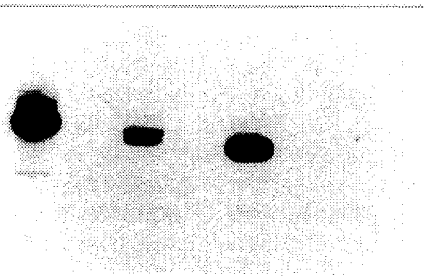
FIG. 10C

E6 ASSOCIATED PROTEIN AND METHODS OF USE THEREOF

BACKGROUND OF THE INVENTION

The present invention relates generally to factors associated with inactivation of tumor suppressor proteins. More particularly, the present invention provides compositions and methods for screening of viruses for carcinogenic potential and screening of compounds for the capability of blocking the inhibitory effect of protein E6 on tumor suppressor protein p53.

Malignant transformation of cells has been linked to expression of proteins encoded by oncogenes (Huang et al., *Cell*, 39:79–87 (1984)). Cells may also be transformed by suppression of growth- and replication-inhibiting factors. Suppression of these inhibiting factors may allow unrestrained cell replication and malignant transformation. Lane and Benchimol, *Genes and Devel.*, 4:1–8 (1990). Human protein p53 is one such inhibiting factor.

Many lines of evidence point to the importance of protein p53 in human carcinogenesis. Mutations within the p53 gene are the most frequent genetic aberration thus far associated with human cancer (Vogelstein, *Nature*, 348:681–682 (1990)) and individuals with germ line p53 mutation have an elevated risk of developing cancer (Malkin et al., *Science*, 250:1233–1238 (1990); Srivastava et al., *Nature*, 348:747–749 (1990)). The mutations identified in cancers are generally point mutations which fall within evolutionarily conserved domains and most of these mutated alleles have transforming activity in various cell culture assays (reviewed in Lane and Benchimol, supra and Levine et al., *Nature*, 351:453–456 (1991)).

Although p53 was originally classified as an oncogene, subsequent studies have shown that wild-type p53 actually has growth suppressive and tumor suppressive properties (Finlay et al., *Cell*, 57:1083–1093 (1989); Eliyahu et al., *Proc. Natl. Acad. Sci. USA*, 86:8763–8767 (1989)). Overexpression of wild-type p53 in normal cells or in transformed cells leads to growth arrest at the G1/S border of the cell cycle (Diller et al., *Mol. Cell. Biol.*, 10:5772–5781 (1990); Baker et al., *Science*, 249:912–915 (1990); Martinez et al., *Genes and Devel.*, 5:151–159 (1991)). p53 has been shown to have negative effects on the transcription of various genes (Ginsberg et al., *Proc. Natl. Acad. Sci. USA*, 88:9979–9983 (1991)), as well as to act as a DNA-binding transcriptional transactivator (Kern et al., *Science*, 256:827–830 (1992); Funk et al., *Mol. Cell. Biol.*, in press (1992); Farmer et al., *Nature*, 358:83–86 (1992)).

p53 was originally identified as a protein that co-immunoprecipitated with large T antigen from SV40 transformed cells (Lane and Crawford, *Nature*, 278:261–263 (1979); Linzer and Levine, *Cell*, 17:43–52 (1979)). It was subsequently shown that the E1B 55 kD protein of adenovirus 5 and the E6 protein of human papillomavirus (HPV) types 16 and 18 can also associate with wild-type p53 (Sarnow et al., *Cell*, 28:387–394 (1982); Werness et al., *Science*, 248:76–79 (1990)). It is believed that the interaction of these viral proteins with p53 aids in releasing infected cells from a block in the cell cycle, resulting in the replication of both the cellular and viral genomes. Additional cellular proteins are involved in transformation as mediated by these viruses, the best characterized being the retinoblastoma tumor suppressor protein (pRB). SV40 large T antigen, the adenovirus E1A proteins, and the anogenital-specific HPV E7 proteins each bind to pRB (Whyte et al., *Nature*, 334:124–129 (1988); DeCaprio et al., *Cell*, 58:1085–1095 (1988); Dyson et al., *Science*, 243:934–937 (1989); Münger et al., *EMBO J.*, 8:4099–4105 (1989)).

The E6 oncoproteins of the cancer-associated or "high risk" human papillomaviruses (HPVs) target cellular p53 protein. The association of E6 with p53 leads to the specific ubiquitination and degradation of p53. This suggests that E6 deregulates cell growth control by eliminating the p53 tumor suppressor protein. Complex formation between E6 and p53 is required for degradation of p53. An additional cellular factor, designated E6-Associated Protein ("E6-AP"), which has a native and subunit molecular mass of approximately 100 kd is necessary for E6-p53 complex formation. Huibregtse et al., *EMBO J.*, 13:4129–4135 (1991).

The HPVs that infect the anogenital tract can be classified as either "high risk" or "low risk" based on their association with cancer. HPV types 16 and 18 are the most common of the high risk group, while HPV type 6 and 11 are among the low risk types. Approximately 90% of cervical cancers contain HPV DNA of the high risk types, and these same DNAs are found in the precancerous epithelial lesions (zur Hausen and Schneider, "The Role of Papillomaviruses in Human Anogenital Cancer", in *The Papovaviridea*, Vol. 2, Plenum, New York, 1987; Riou et al., *Lancet*, 335:1171–1174 (1990)). The low risk types are associated primarily with benign lesions such as condyloma acuminata and are only rarely found associated with cancers. Transfection of DNA of the high risk HPVs results in the extended life span and immortalization of primary human keratinocytes and fibroblasts in cell culture, whereas DNA of the low risk types does not (Dürst et al., *Oncogene*, 1:251–256 (1987); Pirisi et al., *J. Virol.*, 61:1061–1066 (1987); Schlegel et al., *EMBO J.*, 7:3181–3187 (1988)). Mutational analyses have shown that the E6 and E7 genes of the high risk HPVs are both necessary and sufficient for this activity in keratinocytes and fibroblasts (Hawley-Nelson et al., *EMBO J.*, 13:4129–4135 (1989); Münger et al., *J. Virol.*, 63:4417–4421 (1989); Watanabe et al., *J. Virol.*, 63:965–969 (1989)). The specific interactions of the E6 and E7 proteins with p53 and pRB, respectively, correlate with the high and low risk classification. The high risk HPV E7 proteins bind to pRB with a higher affinity than the low risk HPV E7 proteins (Münger et al., *EMBO J.*, supra), and only the high risk HPV E6 proteins form detectable complexes with p53 in vitro (Werness et al., supra).

A striking difference between HPV immortalized cells and adenovirus 5 or SV40 immortalized cells is that the p53 levels are low in HPV containing cells (Scheffner et al., *Proc. Natl. Acad. Sci. USA*, 88:5523–5527 (1991)) but greatly elevated in Ad5 and SV40 immortalized cells (Oren et al., *Mol. Cell. Biol.*, 1:101–110 (1981); Reich et al., *Mol. Cell. Biol.*, 3:2143–2150 (1983)). The low p53 levels in HPV immortalized cells may be explained by the observation that complex formation between E6 and p53 in an in vitro rabbit reticulocyte system leads to the ubiquitination and proteolytic degradation of p53 (Scheffner et al., *Cell*, 63:1129–1136 (1990)). E1B (55 kd) and SV40 large T, on the other hand, sequester p53 into stable complexes (Oren et al., supra; Reich et al., supra). In each case the effect of the viral oncoprotein is to functionally inactivate p53, which apparently leads to cellular proliferation.

Further evidence that the HPV E6 and E7 proteins functionally inactivate the p53 and pRB gene products comes from studies that have examined the state of the p53 and pRB genes in HPV-containing and HPV-negative cervical carcinoma cell lines (Scheffner et al., supra, 1991; Crook et al., *Oncogene*, 6:873–875 (1991); Wrede et al., *Mol. Carcin.*, 4:171–175 (1991)). HPV-containing cell lines were found to express wild-type p53 and pRB, whereas cell lines lacking HPV DNA contained mutations within both the p53 and RB genes. This indicates that inactivation of the p53 and pRB gene products is an important step in cervical carcinogenesis, and that this can occur either by mutation or as a consequence of their interaction with the HPV E6 and E7 proteins.

A means to inhibit degradation of p53 would provide an approach to block the carcinogenic potential of HPVs which inactivate p53 by targeting its degradation. Further, identification of the E6 of a "high risk" HPV in tissue samples would also provide a means for detecting high risk HPV in biopsy samples. What is also needed in the art are means of rapidly and specifically identifying the presence of high risk HPV and of blocking the effects of high risk E6. Quite surprisingly, the present invention fulfills these and other related needs.

SUMMARY OF THE INVENTION

The present invention provides compositions comprising isolated and purified E6 Associated Protein or a polypeptide fragment thereof. Amino acid sequences are provided for polypeptides having E6 Associated Protein binding activity.

Also provided are DNA constructs encoding E6 Associated Protein, or a fragment thereof, which comprise the following operably linked elements: a transcriptional promoter, a DNA sequence encoding E6 Associated Protein or a polypeptide fragment thereof, and a transcriptional terminator. Nucleic acid sequences encoding E6 Associated Protein are provided for use in the DNA constructs.

Methods for detecting human papillomavirus associated with a high risk of malignancy in a biological sample are also provided. The methods generally comprise contacting the sample with a composition comprising mammalian tumor suppressor protein p53 and purified E6 Associated Protein under conditions conducive to complex formation, detecting formation of complexes between E6 and p53 therein, and determining the presence of human papillomavirus infection associated with a high risk of malignancy. The present invention also provides methods for identifying compounds which inhibit binding of E6 to p53. The methods generally comprise contacting compounds of interest with isolated and purified E6-AP to form a mixture, adding the mixture to a composition comprising E6 and p53, but not containing E6 Associated Protein, and detecting formation of complexes of E6 and p53.

Compositions for inhibiting binding of E6 to p53 are also provided. The compositions comprise polypeptides capable of competitively inhibiting binding between E6 and E6-AP. These polypeptides do not bind p53 and thus protect p53 from E6 induced ubiquitination. Nucleic acid sequences comprising these peptides are also provided as well as methods of using the peptides and nucleic acid sequences.

BRIEF DESCRIPTION OF THE DRAWINGS

FIGS. 1A and 1B illustrate a scheme for chromatographic purification of E6-AP.

FIGS. 10A–D illustrate binding of mutant E6-AP proteins with p53.

FIG. 13 illustrates a schematic representation of functional and binding regions of E6-AP.

DESCRIPTION OF THE SPECIFIC EMBODIMENTS

Figure 1B:
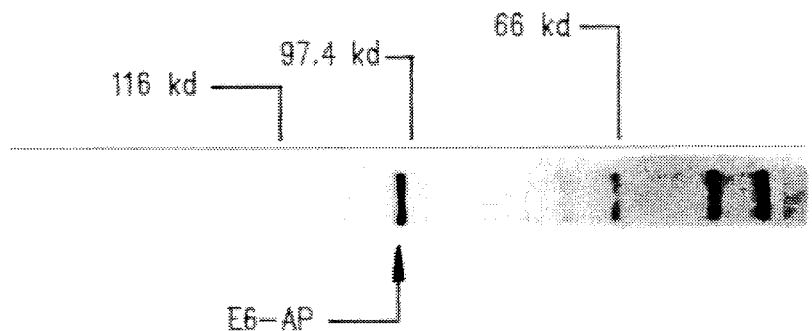

The interaction between E6 of high risk human papillomaviruses, e.g., HPV16 or HPV18, and p53 requires an additional cellular protein, designated E6-AP. The present invention provides purified and isolated forms of E6-AP, DNA constructs encoding E6-AP, and methods of using these compositions. Isolated E6-AP may be used to screen compounds for the potential to inhibit binding between E6 and p53. The purified protein may also be employed to detect the presence of "high risk" human papillomaviruses in biological samples.

The present invention provides isolated and purified E6-AP and fragments thereof. By "E6 Associated Protein" ("E6-AP"), it is meant a polypeptide which has at least one of the following properties: (1) stably associates with wild-type p53 in the presence of HPV16 E6, (2) stimulates the association of HPV16 E6 with p53, or (3) can stably associate with the high risk HPV E6 proteins in the absence of p53. The polypeptide may be naturally occurring or artificially synthesized. Generally, the E6-AP polypeptides will be at least about 6 to 25 amino acids in length, usually more than 100–200 amino acids in length, and more usually more than about 400 amino acids in length, up to and including the sequence of the complete E6-AP protein as set forth in SEQ ID NO:1. The polypeptides of the present invention will generally be homologous to an amino acid sequence of human E6-AP proteins or fragments thereof, such as provided in SEQ ID NO:1, SEQ ID NO:2, SEQ ID NO:3, or fragments thereof. As used herein, "homologous" is meant to include sequences which have at least about 65% relatedness, preferably at least 75% homology, and more preferably at least about 85–90% or more homology to the amino acid sequence of a human E6-AP protein or polypeptide fragment thereof, of the present invention and still retain at least one biological activity of the native protein. As used herein, by "biological activity of an E6-AP polypeptide", it is meant the ability of the polypeptide to (1) stably associate with wild-type p53 in the presence of HPV16 E6, (2) to stimulate the association of HPV16 E6 with p53, or (3) to stably associate with the high risk HPV E6 proteins in the absence of p53. Generally, the proteins and fragments of the present invention will contain an amino acid subsequence homologous to SEQ ID NO:3. Thus, it should be understood that the polypeptide compositions of the present invention need not be identical to any particular E6-AP protein or amino acid sequence thereof, so long as the subject polypeptides have biological activity. Unless otherwise indicated, the term "E6 Associated Protein" or "E6-AP" will include homologs and fragments thereof having at least one biological activity of an E6 Associated Protein.

For example, the polypeptides of interest may be modified by introducing conservative or nonconservative substitutions in the polypeptides, usually fewer than 20 percent, more usually fewer than 10 percent of the amino acids being exchanged. It may be desirable to vary one or more particular amino acids to bind more effectively the E6, p53, or both, for example.

Therefore, the subject polypeptides may be subject to various changes, such as insertions, deletions and substitutions, either conservative or nonconservative, where such changes might provide for certain advantages in their use. "Conservative substitutions" is intended to include, for example, combinations such as gly, ala; val, ile, leu; asp, glu; asn, gln; ser, thr; lys, arg; and phe, tyr. Usually, the sequence will not differ by more than 20% from the sequence of an E6-AP polypeptide or amino acid subsequence thereof.

In addition, the polypeptide sequence may differ from the natural sequence in the modification of the terminal $NH_2$ by acylation, e.g., acetylation, or thioglycolic acid amidation, terminal carboxy amidation, e.g., ammonia, methylamine, etc. In some instances, these modifications may provide increased metabolic stability, decreased immunogenicity or the like, as desired.

These E6-AP peptides of the present invention may be employed to inhibit binding of high risk E6 proteins to p53. By "high risk E6 proteins", it is meant E6 proteins produced by papillomaviruses associated with a high risk of malignant degeneration following cellular infection. Such "high risk E6 proteins" include E6 proteins from human papillomaviruses 16 or 18. Peptides of the present invention may be synthesized which will bind E6, p53, or both. This may block the E6 mediated degradation of p53. Further, E6-AP proteins having mutations in regions necessary for p53 degradation by ubiquitination may be synthesized to block p53 ubiquitination.

Other compounds which inhibit binding between E6 and p53 may be identified in screening assays. A variety of assay formats will suffice and will be readily apparent to the skilled artisan. For example, in one such screening assay the compound of interest is contacted with isolated and purified E6-AP. The mixture of the compound and E6-AP is then added to a composition containing E6 and p53 which does not contain E6-AP. Detection and quantification of labelled E6-p53 complexes provides a means for determining the compound's efficacy at inhibiting complex formation between E6 and p53. Conveniently, a control assay is also performed to provide a baseline for comparison. In the control assay, isolated and purified E6-AP is added to a composition containing E6 and p53. E6-p53 complex formation is quantitated. As will be well understood by persons of skill in the art, the various amounts and concentrations of E6-AP, E6 and p53, as well as the reaction conditions in the control assays are generally similar if not identical to those in the screening assay.

Complex formation between E6 and p53 may be detected by a variety of methods. For example, glutathione S-transferase-p 53 fusion proteins are adsorbed onto glutathione sepharose beads which are then combined with $^{35}S$-labeled E6 protein and incubated under conditions conducive to complex formation, e.g., at 4° C. in a buffer of 25 mM Tris-HCl (pH 7.2), 50 mM NaCl and 0.2% NP-40. Following incubation, the beads are washed and the complexes dissociated. Incubation is generally performed over a period of 2–6 hours. The supernatant containing the complexes is loaded onto a SDS-Page gel. The complexes may then be identified, excised, and eluted from the gel. The amount of radioactivity in the complex containing fractions indicates the amount of complex formation in between E6 and p53. See also, Huibregtse et al., *EMBO J.,* 10:4129–4135 (1991), incorporated herein by reference.

Peptides of the present invention may also be employed to detect the presence of "high risk human papilloma viruses" in tissue samples. By "high risk human papillomaviruses", it is meant that the virus is associated with a high risk of malignant degeneration of infected cells. These include human papillomaviruses 16 and 18 and may include types 31, 33, 35, 45, 51, 52, and 56. The E6-AP proteins of the present invention selectively bind to E6 proteins of high risk human papillomaviruses. Therefore, detection of binding of a peptide of the present invention to a protein in a tissue sample provides a means for identifying samples containing high risk E6-AP protein, and hence high risk human papillomaviruses, in the tissue.

Detection of binding between E6-AP or homologs or fragments thereof of the present invention and high risk E6 in tissue samples may be detected by a variety of methods. In situ binding between labeled E6-AP and high risk E6 may be employed to detect the high risk E6 protein. Tissue samples are fixed by standard methods. For example, E6-AP peptides of the present invention are labeled, such as by iodination as described for antibodies in Sambrook et al., *Molecular Cloning, A Laboratory Manual,* Cold Spring Harbor Laboratory Press, 1989, incorporated herein by reference. The labeled E6-AP is incubated with the fixed tissue and then washed. Bound labeled E6-AP is then identified by means appropriate for the label, e.g., by autoradiography for iodinated E6-AP. Binding of E6-AP to the tissue indicates the presence of high risk E6 proteins, and therefore the presence of high risk human papillomaviruses in the tissue. Identification of high risk human papillomaviruses in the tissue provides a means for determining groups of patients which require further treatment or more intensive follow-up.

Another method for identifying E6-AP proteins or peptides of the present invention is targeted mutagenesis. DNA sequences encoding the polypeptides are mutated by recombination with randomly or site-directed mutated oligonucleotides derived from the native sequence. The mutated genes are then expressed in a host cell which can express the polypeptide, and then assayed for binding to high risk E6 or p53. Mutants which bind high risk E6 protein or p53 are compared to the native sequence and the specific mutation is identified. The location of the mutation may identify the functional and binding domains of the native proteins. Smaller peptides may be designed which mimic the binding or functional domains of the native protein. The smaller peptides may be synthesized by standard techniques as described herein and screened in a manner similar to the mutated polypeptides.

Polypeptides which are substantially complementary to the amino acid sequences of E6-AP peptides of the present invention, such as SEQ ID NO:1, SEQ ID NO:2, or SEQ ID NO:3, or fragments thereof, may be produced by a variety of methods. Shorter polypeptides, generally in the range of about 10 to about fifty amino acids, may be synthesized in solution or on a solid support in accordance with conventional techniques. See, e.g., Stewart and Young, *Solid Phase Polypeptide Synthesis,* 2nd edition, Pierce Chemical Company, 1984; and Tam, et al., *J. Am. Chem. Soc.,* 105:6442, 1983, both of which are incorporated herein by reference.

Alternatively, hybrid DNA technology may be employed for expression of the desired polypeptide in transformed eukaryotic or prokaryotic host cells, particularly when the polypeptide is a full length E6-AP or substantial portion thereof. See, e.g., Sambrook et al., supra. Procaryotes may be employed for cloning and expressing DNA sequences to produce E6-APs for use in the present invention. Several methods may be employed to produce the desired polypeptides such as those described in Sambrook et al., supra.

Several different procaryotic hosts are suitable for cloning the desired DNA sequences. For example, *E. coli* K12 strain 294 (ATCC No. 31446) is particularly useful. Other microbial strains which may be used include *E. coli* strains such as *E. coli* B, and *E. coli* X1776 (ATCC No. 31537), and *E. coli* c600 and c600hfl, *E. coli* W3110 (F⁻,λ⁻, prototrophic, ATCC No. 27325), bacilli such as *Bacillus subtilus,* and other enterobacteriaceae such as *Salmonella typhimurium* or *Serratia marcescens,* and various Pseudomonas species. When expressed in procaryotes the polypeptides used in the present invention typically contain an N-terminal methionine or a formyl methionine, and are not glycosylated. These examples are, of course, intended to be illustrative rather than limiting.

The present invention also provides DNA constructs encoding E6-AP or fragments thereof. The DNA constructs generally comprise a transcriptional promoter, a DNA sequence encoding E6-AP or a fragment thereof, and a transcriptional terminator. Exemplary DNA sequences encoding E6-AP proteins, homologs or fragments thereof include SEQ ID No:4, SEQ ID No:5, and SEQ ID No:6.

In general, plasmid vectors containing replication and control sequences which are derived from species compatible with the recombinant host cells are used in connection with these hosts. Other vectors, such as λ-phage, cosmids, or yeast artificial chromosomes may be employed. The vector ordinarily carries a replication site, as well as sequences which encode proteins that are capable of providing phenotypic selection in transformed cells. For example, *E. coli* may be transformed using pBR322, a plasmid derived from an *E. coli* species. Plasmid pBR322 contains genes for ampicillin and tetracycline resistance and thus provides easy means for identifying and selecting transformed cells. The pBR322 plasmid, or microbial plasmid must also contain, or be modified to contain, promoters which can be used by the microbial organism for an expression of its own proteins. Those promoters most commonly used in recombinant DNA construction include β-lactamase (penicillinase) and lactose promoter systems and a tryptophan (trp) promoter system. One suitable promoter is contained in the in vitro transcription vector pGEM-1. The promoter is a T7 and SP6 polymerase promoter. While these are the most commonly used, other microbial promoters have been discovered and utilized, and details concerning their nucleotide sequences have been published, enabling a skilled worker to ligate them functionally with plasmid vectors. The promoters are operably linked to a nucleic acid sequence encoding an E6-AP or a homolog or fragment thereof. The promoters may be inducible or constitutive and provide a means to express the encoded E6-AP in the procaryotic host. Following expression, the polypeptide may be purified by standard methods such as described below.

Alternatively, a DNA sequence encoding E6-AP protein or homolog or fragment thereof may be inserted into a suitable eukaryotic expression vector, which in turn is used to transfect eukaryotic cells. A eukaryotic expression vector, as used herein, is meant to indicate a DNA construct containing elements which direct the transcription and translation of DNA sequences encoding polypeptides of interest. Such elements include promoters, enhancers, transcription terminators and polyadenylation signals. By virtue of the inclusion of these elements operably linked within the DNA constructs, the resulting eukaryotic expression vectors contain the information necessary for expression of the polypeptides of interest.

Host cells for use in expressing recombinant E6-AP polypeptides of interest include mammalian, avian, insect and fungal cells. Fungal cells, including species of yeast (a.g., Saccharomyces spp., Schizosaccharomyces spp.) or filamentous fungi (e.g., Aspergillus spp., Neurospora spp.) may be used as host cells for producing polypeptides useful in the present invention. Suitable vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources. The expression units may also include a transcriptional terminator. Choice of a particular host and selectable marker is well within the level of ordinary skill in the art.

Cultured mammalian cells may be used as host cells within the present invention. Cultured mammalian cells for use in the present invention may include human monocytoid, lymphocytoid, and fibroblastoid cell lines. A preferred mammalian cell line is the HeLa-tat cells that are HeLa derived cells which produce constitutively HIV-1 Tat (Schwartz et al., supra). Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864, 1981). Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81:7041–7045, 1983); Grant et al., *Nuc. Acids Res.* 15:5496, 1987) and a mouse $V_H$ promoter (Loh et al., *Cell* 33:85–93, 1983).

A particularly preferred promoter is the HIV LTR promoter from HIV-1. Such expression vectors may also contain a set of RNA splice sites located downstream from the promoter and upstream from the DNA sequence encoding the polypeptide or protein of interest. Preferred RNA splice sites may be obtained from adenovirus and/or immunoglobulin genes. Also contained in the expression vectors is a polyadenylation signal located downstream of the coding sequence of interest.

Polyadenylation signals include the early or late polyadenylation signals from SV40 (Kaufman and Sharp, ibid.), the polyadenylation signal from the Adenovirus 5 ElB region and the human growth hormone gene terminator (DeNoto et al., *Nuc. Acids Res.* 9:3719–3730, 1981). The expression vectors may include a noncoding viral leader sequence, such as the AdenoVirus 2 tripartite leader, located between the promoter and the RNA splice sites. Vectors may also include enhancer sequences, such as the SV40 enhancer and the mouse μ enhancer (Gillies, *Cell* 33: 717–728, 1983). Expression vectors may also include sequences encoding the adenovirus VA RNAs.

Cloned DNA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973). Other techniques for introducing cloned DNA sequences into mammalian cells, such as electroporation (Neumann et al., *EMBO J.* 1:841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker such as the DHFR gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods for introducing expression vectors encoding E6-AP polypeptides are well known in the art. Host cells containing DNA constructs of the present invention are then cultured according to standard methods to produce the E6-AP polypeptides. The growth medium will generally select for cells containing the DNA construct by, for example, drug selection or deficiency of an essential nutrient which is complemented by the selectable marker on the DNA construct or co-transfected with the DNA construct.

The E6-AP polypeptides produced according to the present invention, either authentic (native) or recombinant polypeptides, may be purified by a variety of means, including via affinity chromatography, e.g., on an antibody column using antibodies directed against the E6-AP polypeptide or using E6-AP binding substances. Additional purification may be achieved by conventional chemical purification means, such as liquid chromatography, gradient centrifugation, and gel electrophoresis, among others. Methods of protein purification are known in the art (see generally, Scopes, R., *Protein Purification*, Springer-Verlag, N.Y. (1982), which is incorporated herein by reference) and may be applied to the purification of the recombinant E6-AP protein described herein; see also a purification protocol described in U.S. Pat. No. 4,929,604, incorporated herein by reference. FIG. 1 illustrates a particularly effective method of purification of E6-AP. Briefly, cells expressing E6-AP are lysed. The lysate is sequentially loaded into four connected chromatographic columns, generally a Bio-Rad -CM, a Bio-Rad S, and two Bio-Rad Q columns. Fractions eluted from the Q columns and containing E6-AP are pooled and dialyzed. The resulting solution is loaded onto a Bio-Rad Heparin column and eluted with a NaCl gradient. E6-AP fractions are again dialyzed and loaded onto to a Bio-Rad DEAE Blue column. Retained E6-AP is eluted with a NaCl gradient and loaded onto a Pharmacia Mono Q column. Peak E6-AP fractions from the Mono Q columns are pooled, concentrated, and separated by SDS-PAGE.

Substantially pure E6-AP polypeptide of at least about 50% is preferred, at least about 70–80% more preferred, and 95–99% or more homogeneity most preferred, particularly for pharmaceutical uses. Once purified, partially or to homogeneity, as desired, the E6-AP polypeptide may then be used therapeutically, diagnostically, or in screening assays as described herein.

The purified polypeptides may then be combined in pharmaceutical compositions for a variety of therapeutic uses. The compositions may be administered to persons or animals infected by high risk human papilloma viruses. The polypeptide in the pharmaceutical composition can bind p53, E6, or both and inhibit p53 degradation. The concentration of the purified peptides in these formulations can vary widely, i.e., from less than about 0.5%, usually at or at least about 1% to as much as 15 or 20% by weight and will be selected primarily by fluid volumes, viscosities, etc., in accordance with the particular mode of administration selected. Actual methods for preparing parenterally administrable compounds will be known or apparent to those skilled in the art and are described in detail in, for example, Remington's Pharmaceutical Science, 17th ed., Mack Publishing Company, Easton, Pa. (1985), which is incorporated herein by reference.

Preferably, the pharmaceutical compositions are administered parenterally, i.e., intravenously, subcutaneously, or intramuscularly. Thus, this invention provides compositions for parenteral administration which comprise a solution of an inhibitory peptide of the present invention or dissolved in a pharmaceutically acceptable carrier, preferably an aqueous carrier. A variety of aqueous carriers can be used, e.g., water, buffered water, 0.9% saline, 0.3% glycine, and the like, including glycoproteins for enhanced stability, such as albumin, lipoprotein, globulin, etc. In some instances such as treating neurological malignancies, it can be desirable to package the prodrugs in liposomes for administration. These compositions can be sterilized by conventional, well known sterilization techniques. The resulting aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such an pH adjusting and buffering agents, tonicity adjusting agents and the like, for example, sodium acetate, sodium lactate, sodium chloride, potassium chloride, calcium chloride, etc. Appropriate dosage ranges and routes of administration can be determined by standard techniques as described in Remington's Pharmaceutical Science, 17th ed., Mack Publishing Company, Easton, Pa. (1985), previously incorporated herein by reference.

E6-AP fusion proteins may also be constructed by fusion of nucleic acid encoding E6-AP, or fragments thereof, to nucleic acid sequences encoding protein binding polypeptides. The resulting fusion proteins could provide a means for selectively binding E6-AP to target proteins. The target proteins could then be subject to E6-AP induced degradation by ubiquitination.

The following examples are offered by way of illustration, not by way of limitation.

Example 1

This example describes isolation and purification of E6-AP. The protein was isolated to sufficient purity for N-terminal sequencing of peptide fragments of the protein. FIG. 1 illustrates the purification scheme.

Saos-2 cells (A.T.C.C. No. HTB 85), which were derived from an osteosarcoma and contain a homozygous deletion of the p53 gene (Diller et al., 1990, supra), were used as a source for purification of E6-AP. The cells were maintained in Dulbecco's modified Eagle's medium containing 10% fetal calf serum (Gibco). Cell extract was made from 270 176 cm² plates of confluent cells by lysing the cells on each plate in 2 ml lysis buffer (0.1M Tris-HCl, pH 7.4, 0.1M NaCl, 1% NP-40, 1 mM DTT, 0.01% PMSF, and 1 µg/ml aprotinin and leupeptin). The plates were scraped and insoluble material removed by centrifugation for 10 min. at 10,000×g at 4° C. The extract was divided into three aliquots and the chromatographic procedures described below were performed on each. All chromatographic procedures were performed using a Pharmacia FPLC system. The assay of column fractions for E6-AP activity was based on the ability of E6-AP to stimulate the binding of $^{35}$S-labeled wheat germ extract translated HPV16 E6 to sepharose beads containing GST-p53 by the method of Huibregtse et al., *EMBO J.*, 13:4129–4135 (1991), incorporated herein by reference. p53 was purified from *E. coli* as a glutathione S-transferase fusion protein (GST-p53) and a wheat germ extract translation system was used to synthesize $^{35}$S-methionine labeled E6 protein. The wheat germ extract translation system was used because it does not contain E6-AP activity.

Each extract was loaded onto a series of four connected BioRad Econo-Pac columns arranged in the following order: BioRad-CM, S, and two Q columns. The columns were equilibrated with 25 mM Tris-HCl, pH 7.4, 100 mM NaCl, and 1 mM DTT. After loading, the columns were washed thoroughly with the equilibration buffer and then the CM and S columns were removed. Proteins bound to the Q columns were eluted with a 60 ml linear salt gradient to 500 mM NaCl. Fractions eluting at approximately 250 mM NaCl contained E6-AP activity and were pooled and dialyzed against 25 mM Tris-HCl, pH 7.4, 50 mM NaCl, and 1 mM DTT. This was loaded onto a BioRad Heparin column equilibrated at 50 mM NaCl. A 50 ml linear gradient to 500 mM NaCl was used to elute bound protein. E6-AP activity eluted at approximately 225 mM NaCl. E6-AP containing fractions were dialyzed against 25 mM Tris-HCl, pH 7.4, 50 mM NaCl, 1 mM DTT and loaded onto a BioRad DEAE Blue column equilibrated in the same buffer.

Figure 2:
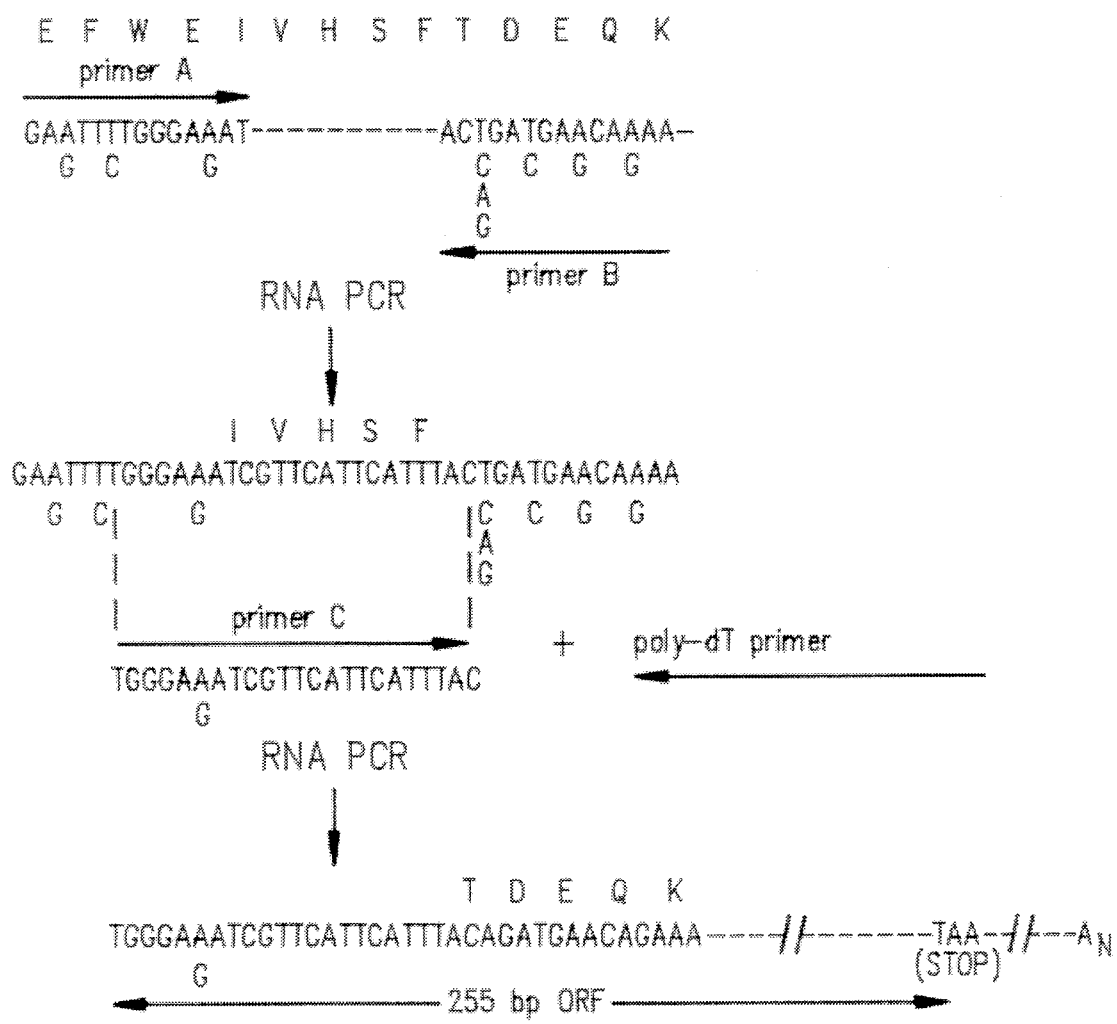
FIG. 2 illustrates a strategy for isolation of E6-AP-encoding cDNA by RNA PCR.

E6-AP activity was retained in the column and was eluted with a linear salt gradient to 500 mM NaCl. Peak fractions were dialyzed against 25 mM Tris-HCl, pH 7.4, 125 mM Nacl, 1 mM DTT and loaded onto a Pharmacia Mono Q column. E6-AP activity was eluted at approximately 325 mM NaCl with a linear salt gradient to 400 mM NaCl. Several proteins were evident in the most purified E6-AP fractions by silver staining, with the predominant species migrating with an apparent molecular mass of approximately 100 kd (FIG. 2). This was consistent with the molecular mass of E6-AP as determined previously (Huibregtse et al., 1991). Peak E6-AP fractions from the Mono Q columns were pooled and concentrated in an Amicon centricon-10 filtration unit and loaded into a single lane of a 7.5% SDS polyacrylamide gel.

Following electrophoresis the gel was soaked in western transfer buffer (12.5 mM Tris, pH 8.3, 100 mM glycine) for 10 min. and then electroblotted to nitrocellulose (Schleicher and Schuell, 0.45 µm) at 40 volts for 2 hrs. The blot was stained with 0.1% Ponceau S (Sigma) in 1% acetic acid for 1 min. The blot was destained with 1% acetic acid, rinsed in water, and a 24 mm² section corresponding to an approximately 100 kd protein was excised from the blot. The protein was eluted from the blot and subjected to tryptic digestion. The resulting peptides were isolated by HPLC. Each of the peptides was then partially sequenced. The N-terminal sequences of five peptides were determined by automated Edmann degradation chemistry.

Example 2

This example illustrates isolation and cloning of cDNA encoding E6-AP.

Degenerate oligonucleotide primers were synthesized corresponding to the amino-terminal and carboxy-terminal ends of one of the peptide sequences as shown in SEQ ID NO:1. These primers were used in a polymerase chain reaction (PCR) using random-primed reverse transcribed cytoplasmic RNA. Lambda clones were isolated from a random-primed cDNA library made from polyadenylated RNA isolated from normal human foreskin keratinocytes (Clontech). The RNA was isolated from normal primary human keratinocytes. Polyadenylated RNA was prepared using an Invitrogen FastTrack mRNA isolation kit and PCR was performed using a Cetus RNA PCR kit. All PCR products were cloned into pGEM-1A (Promega) and sequenced using a United States Biochemicals Sequenase kit. 51 bp PCR product was isolated, cloned, and sequenced. The DNA sequence between the oligonucleotide primers encoded the amino acids predicted by the peptide sequence. From this sequence information a 26 nucleotide primer containing a single degeneracy was synthesized. To obtain a clone that extended to the 3'-end of the cDNA, the 26 nucleotide primer was used with an oligo dT primer in a second round of PCR, again using reverse transcribed cytoplasmic RNA as template. A fragment of approximately 320 bp was isolated, cloned, and sequenced. The 320 bp sequence contained a 255 bp open reading frame (ORF). A putative polyadenylation site (AAUAAA) was located 16 bp downstream of the translation stop codon, which was followed by a stretch of 20 adenines 17 bp further downstream, indicating that this clone probably represented the 3'-end of the cDNA for this gene.

The 255 bp fragment corresponding to the 3'-end of the putative E6-AP ORF was used to probe a random-primed cDNA library made from polyadenylated RNA isolated from primary human keratinocytes (Clontech). $^{32}$P-labeled DNA probes were prepared using a BRL random primers labeling kit and $^{32}$p-a-dCTP (Amersham). Inserts from lambda clones were subcloned into pGEM-1A by first isolating the insert by PCR using primers flanking the lambda gt11 cloning site. Several positive lambda clones were isolated and sequenced. The first clone isolated from the library contained the exact sequence contained within the probe as well as the same sequence downstream of the translation stop codon. In addition, the clone extended in-frame in the 5' direction for approximately 850 bp and contained sequences encoding each of the other four sequenced peptides. Overlapping lambda clones extending in the 5'-direction were then isolated from the same library. The cDNA sequence shown in SEQ ID No:4 contains only those sequences that were present in multiple independently isolated clones. The cDNA sequence contains an ORF that encodes 865 amino acids with a total predicted molecular mass of 99,289 daltons. This molecular weight closely approximates the predicted molecular mass of E6-AP. The complete ORF was cloned in a single fragment by taking advantage of unique restriction sites within the DNA sequence. Northern analysis using probes within the ORF and polyadenylated RNA isolated from primary human foreskin keratinocytes showed a major hybridizing species of approximately 5 kb. The sequence shown in SEQ ID No:4 plus the 3'-untranslated sequence constitute approximately 2700 bp, meaning that the mRNA for this protein may have a very long 5'-untranslated region, containing perhaps as 2300 nucleotides.

MacVector software (IBI) was used for sequence analysis and GenBank and SwissProt data bases were searched with the FASTA and TFASTA algorithms. The cDNA sequence was not identical to any recorded in DNA or protein data bases. Varying degrees of homology were identified between human E6-AP and other proteins of unknown function, e.g., NEDD4, a mouse protein of unknown function and a rat protein of unknown function. A search for common conserved protein motifs revealed several potential phosphorylation sites (casein kinase 2, protein kinase C), however preliminary evidence suggests that E6-AP is not a phosphoprotein. The encoded protein has a predicted isoelectric point (pI) of 4.95, with the most acidic region being from amino acid 377 to 406, where 13 of 30 amino acids are either aspartic or glutamic acids. The most extensive reiterated amino acid sequence within the protein is NKKG-R-D-D/E, which is found beginning at amino acid positions 104 and 409. This motif was not found in any sequences in DNA or protein data bases. There is no apparent relationship between the E6-AP cDNA and the mdm2 cDNA, which encodes a cellular protein that interacts with both wild-type and at least some mutant forms of p53 (Fakharzadeh et al., *EMBO J.*, 10:1565–1569 (1991); Oliner et al., *Nature*, 358:80–83 (1992); Momand et al., *Cell*, 69:1237–1245 (1992)).

Example 3

This example demonstrates the association of E6-AP with p53 protein. E6-AP was recombinantly produced and isolated from p53-deficient cells. The isolated E6-AP protein was then shown to bind to p53 in the presence of HPV16 E6. Isolated E6-AP was shown to only weakly bind mutant p53, even in the presence of HPV16 E6.

Clones used for in vitro transcription and translation were prepared by PCR of the ORF using a downstream oligonucleotide spanning the translation termination codon and an upstream oligonucleotide containing an in-frame optimal translation initiation codon by the method described in Kozak, *J. Biol. Chem.*, 266:19867–19870 (1991), incorporated herein by reference. In vitro translated proteins were prepared using a wheat germ extract translation system (Promega) and $^{35}$S-labeled methionine (ICN or Amersham).

The complete ORF encodes 865 amino acids as shown in SEQ ID NO:1. Amino acid sequences 544–562, 641–653, 702–714, 754–772, and 779–793 represent the five peptides that were sequenced. The translation stop codon is bp2596–2598. Amino acids 37 and 213 represent the 5'-ends of the cDNAs encoding the 95 and 76 kd translation products, respectively.

The complete ORF shown in SEQ ID NO:1 as well as subclones that extended from bp109 or bp637 to the carboxy-terminus were cloned into an in vitro transcription vector containing an in-frame optimal translation start codon. In vitro synthesized RNA was translated in a wheat germ extract system in the presence of $^{35}$S-labeled methionine. The smaller subclones were translated efficiently and gave rise to the predicted sized proteins of 95 and 76 kd (FIGS. 3 and 4), however the full-length clone was translated poorly and was therefore not used in the experiments described below.

Figure 7:
FIG. 7 illustrates degradation of p53 in the presence of in vitro-translated E6-AP and HPV16 E6.

The 95 and 76 kd in vitro translated proteins were tested for association with p53 by employing essentially the same assay used for assaying column fractions for E6-AP activity. 30 µl of $^{35}$S-labeled in vitro translate was mixed with 10 µl of $^{35}$S-labeled in vitro translate was mixed with 10 µl of $^{35}$S-labeled wheat germ extract translated HPV16 or 11 E6 and 10 µl of glutathione sepharose beads containing approximately 0.2 µg of GST-p53 protein. The mixture also contained 125 µl of 25 mM Tris-HCl (pH 7.4), 50 mM CaCl and 25 µl of lysis buffer (0.1M Tris-HCl, pH 7.4, 0.1M NaCl, 1% NP-40, 1 mM DTT, 0.01% PMSF, and 1 µg/ml aprotinin and leupeptin). Reactions that did not contain added E6 or E6-AP translations had an equivalent amount of a mock translation reaction that was programmed with water. The mixtures were rotated at 4° C. for 4 hrs. The beads were collected by centrifugation, washed 3 times with lysis buffer, boiled in SDS gel loading buffer, and electrophoresed on 12% SDS polyacrylamide gels. Gels were fixed, soaked in Enlightening (Dupont), dried, and exposed to Kodak XAR film. The GST-p53 and GST-mutant p53 (Tyr$_{135}$) plasmids and proteins were prepared as described in Huibregtse et al., *EMBO J.*, 13:4129–4135 (1991), previously incorporated herein by reference. The in vitro transcription/translation plasmids used for synthesizing the E6 proteins were described in Werness et al., *Science*, 248:76–79 (1990), incorporated herein by reference. Gels were scanned using an Ambis radioanalytic imager (FIGS. 3 and 4) or an LKB densitometer (FIG. 7).

Binding of the 95 and 76 kd proteins to GST-E6 proteins was done essentially as described in Example 1. The in vitro translate was mixed with 10 µl of GST, GST-16, 18, 11, or 6 E6 immobilized on glutathione sepharose (approximately 0.2 µg of protein each) along with 125 µl of 25 mM Tris-HCl (pH 7.4), 50 mM NaCl and 25 µl of lysis buffer. The mixtures were incubated for 4 hrs. at 4° C. and bound protein analyzed as described above. The GST-E6 plasmids and proteins were prepared as described in Huibregtse et al., supra, 1991.

In vitro degradation assays were performed by mixing 2 µl of $^{35}$S-labeled wheat germ extract translated p53 with 10 µl of unlabeled HPV16 E6 translate (or an equivalent amount of mock translate), 30 µl of unlabeled 95 or 75 kd protein translate (or an equivalent amount of mock translate), 40 µl of 25 mM Tris-HCl (pH 7.4), 50 mM NaCl, and 2 µl of 2 mg/ml ubiquitin (Sigma). The mixtures were incubated at room temperature for 4 hrs. The p53 was immunoprecipitated with a p53-specific monoclonal antibody (PAb421) as described by Werness et al., supra, and analyzed by SDS-PAGE and autoradiography.

Figure 3:
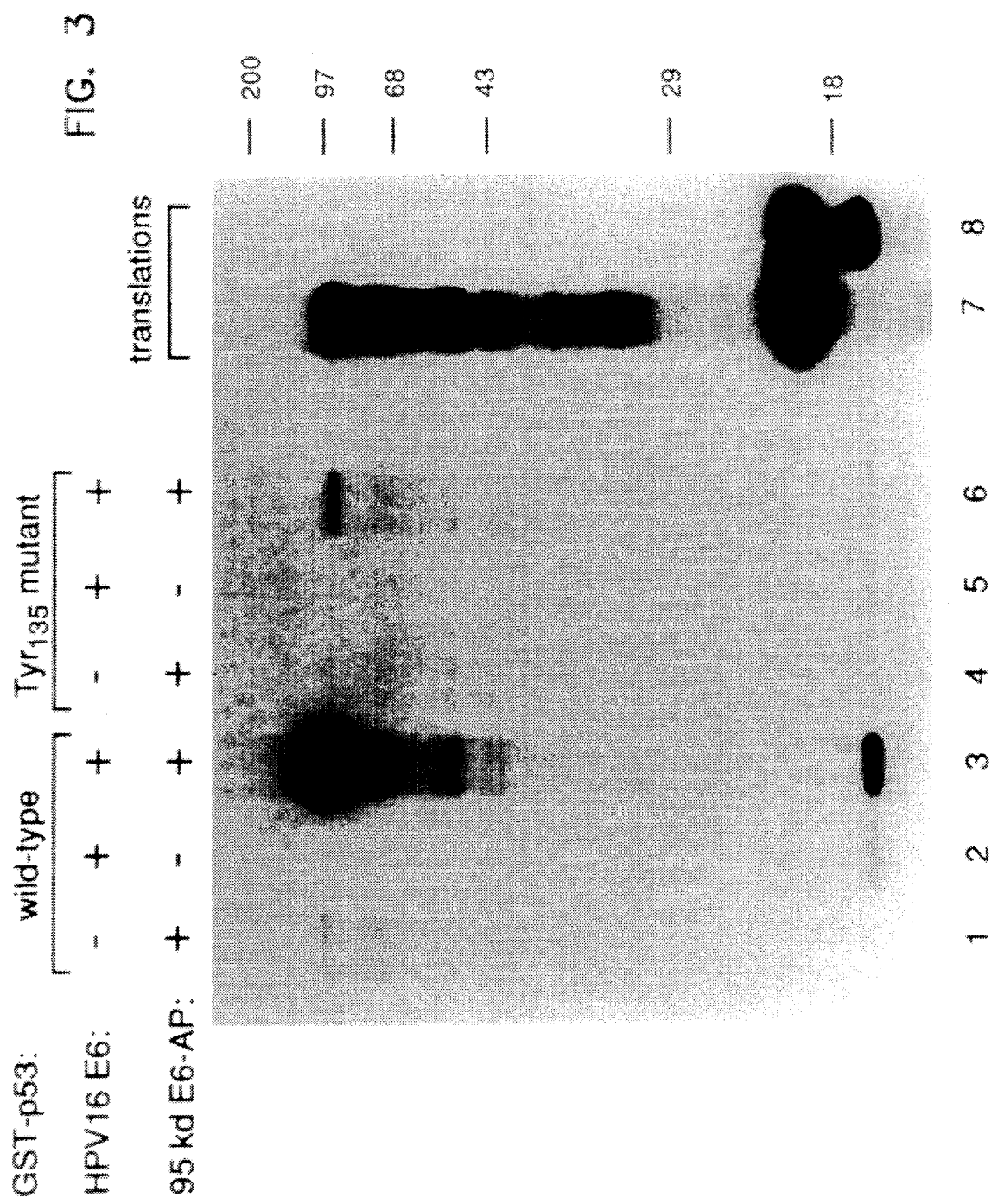
FIG. 3 illustrates binding of wild-type and mutated p53 with E6 and a 95 kd form of E6-AP.

The 95 kd in vitro translated protein was tested for its ability to bind to wild-type or mutant p53 (cys to tyr change at position 135) in the presence or absence of HPV16 E6. FIG. 3 shows that the 95 kd E6-AP protein bound to a low degree when mixed with GST-wild-type p53 in the absence of E6 (lane 1). Similarly, $^{35}$S-methionine-labeled wheat germ extract-translated HPV16 E6 bound to a low degree in the absence of the 95 kd protein (lane 2). When the 95 kd E6-AP and HPV16 E6, translations were mixed together, however, the binding of the 95 kd protein to p53 was dramatically increased (lane 3). This was accompanied by an increase in HPV16 E6 binding, as well. In contrast, binding of the 95 kd protein to the Tyr$_{135}$ mutant of p53 was increased only slightly when mixed with E6 (FIG. 3, lanes 4–6). Association of E6-AP with this mutant form of p53 has been shown to be greatly diminished relative to wild-type p53 (Huibregtse et al., 1991) and HPV16 E6 does not bind or degrade this protein to a detectable degree in vitro (Scheffner et al., 1992b).

The mutual stimulation of binding of E6-AP and E6 to wild-type p53 (FIG. 3, lanes 1–3) was quantitated. Correcting for the number of methionines in each protein (25 in the 95 kd protein and 2 in HPV16 E6), the increase in binding relative to the background levels (lane 3 compared to lane 1 for E6-AP; lane 3 compared to lane 2 for E6) was consistent with a 1:1 ratio of the 95 kd protein to E6 protein in complex with p53. Because the level of binding of the 95 kd E6-AP protein to wild-type p53 seen in the absence of E6 (lane 1) is very similar level of binding to the mutant form of p53 is seen in the absence of E6 (lane 4), the binding of the 95 Kd E6-AP protein to wild-type p53 is non-specific. In addition, the similar levels of E6 binding to wild-type p53 seen in the absence of the 95 kd E6-AP and E6 binding to mutant p53 in the absence of the 95 kd E6-AP protein (lanes 2 and 5) indicates that binding between E6 and p53 in the absence of the 95 kd protein is non-specific.

Figure 4:
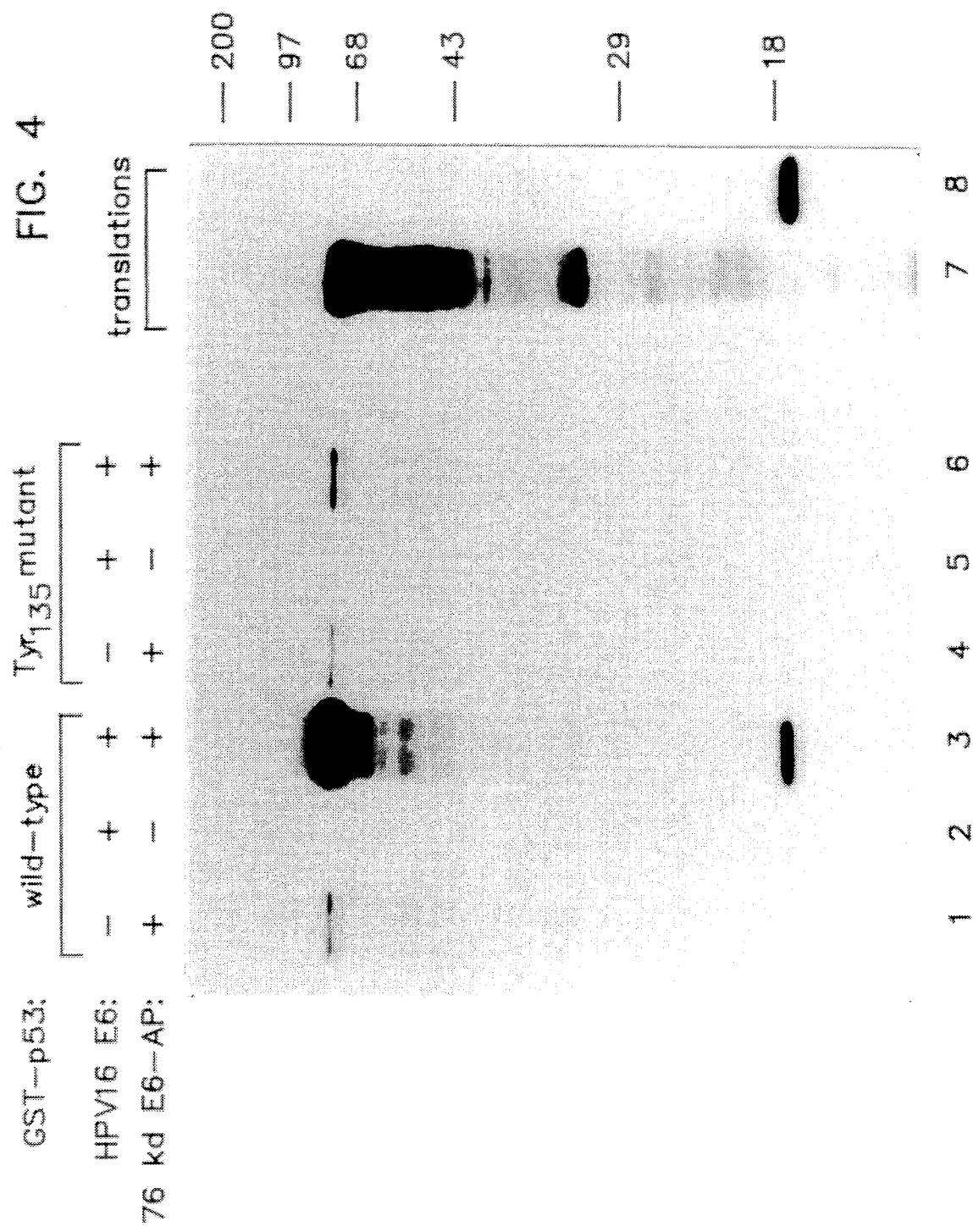
FIG. 4 illustrates relative binding of wild-type and mutated p53 with E6 and a 76 kd form of E6-AP.

The 76 kd in vitro translated form of the putative E6-AP protein was also assayed for p53 binding (FIG. 4). As with the 95 Kd form, the binding of HPV16 E6 and the 76 kd E6-AP protein to wild-type p53 was mutually stimulatory and was not seen with the mutant form of p53. This further suggests that the cloned cDNA does indeed represent E6-AP and that the N-terminal 212 amino acids encoded by the ORF are not required for the p53 binding activity. Quantitation of the signals as described above again indicated roughly a 1:1 ratio of 76 kd E6-AP to E6 protein in complex wild-type p53.

Figure 5:
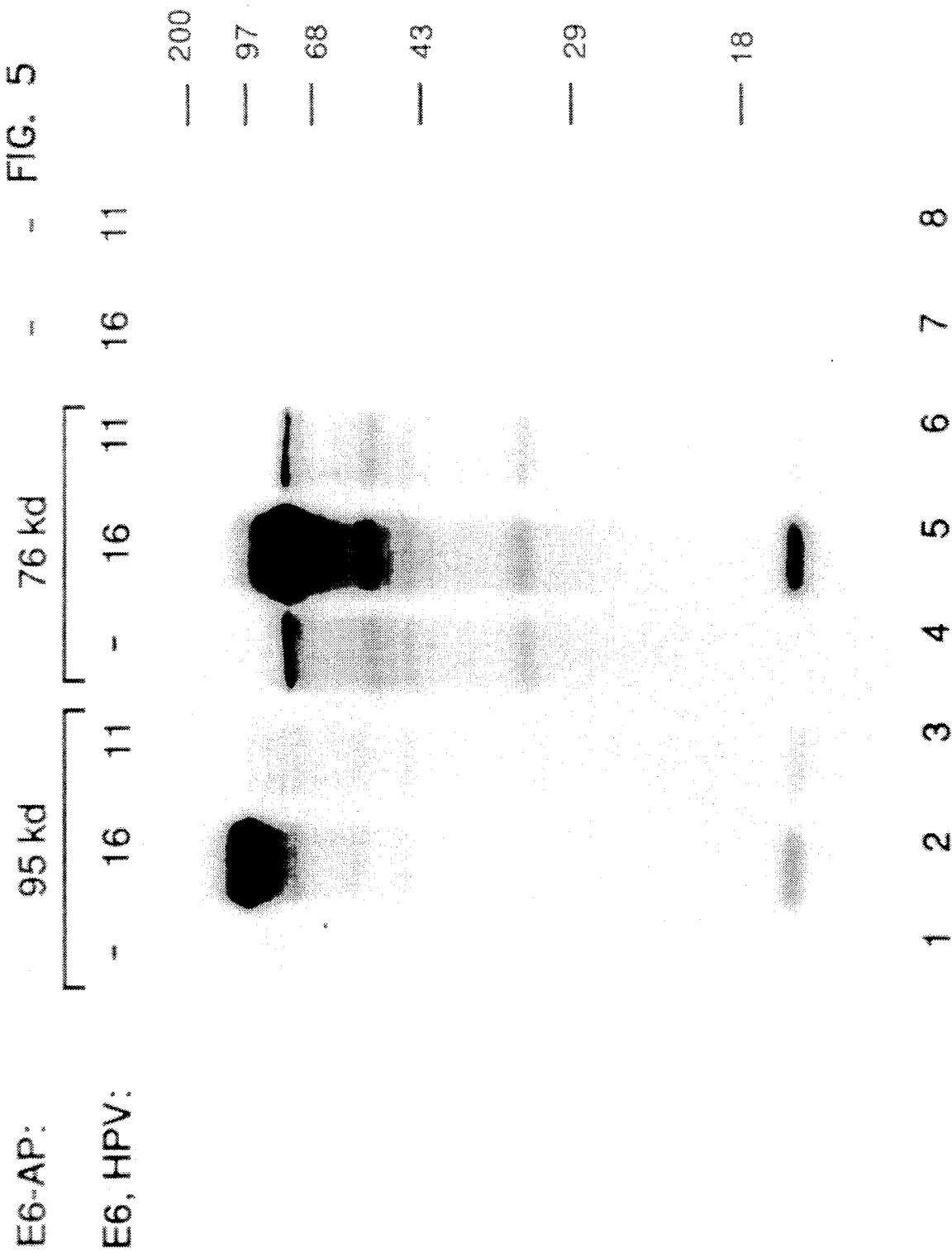
FIG. 5 illustrates association of p53 with HPV16 E6 and HPV11 E6 in the presence of wild-type in vitro-translated E6-AP.

Intracellular E6-AP association with p53 is dependent on the presence of high risk as opposed to low risk HPV E6 proteins. The 95 and 76 kd in vitro translated proteins were therefore tested for their ability to bind to GST-wild-type p53 in the presence of HPV16 versus HPV11 E6 protein. As shown in FIG. 5, stimulation of binding of both forms to p53 was only seen in the presence of HPV16 E6. Binding in the presence of HPV11 E6 was equivalent to the level seen in the absence of E6-AP protein.

Figure 6:
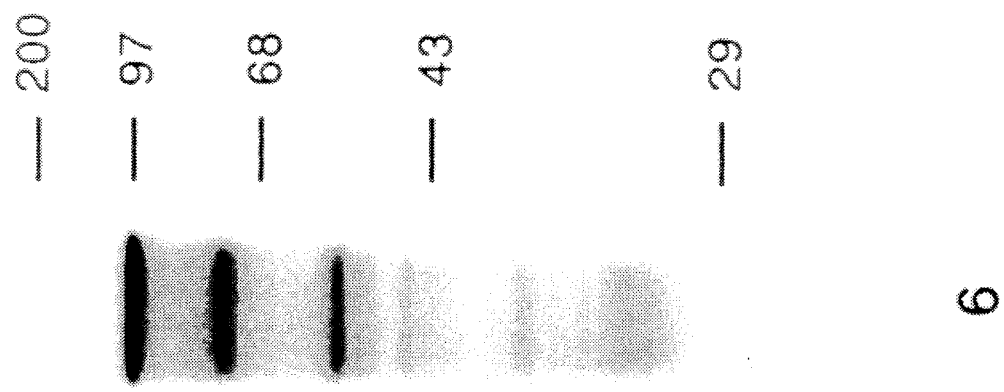
FIG. 6 illustrates association of high- and low-risk HPV E6 proteins to in-vitro translated E6-AP.
Figure 6:

Although E6-AP does not stably associate with p53 in the absence of high risk HPV E6 proteins, it does stably, associate with high risk HPV E6 proteins in the absence of p53. The 95 kd in vitro translated form of E6-AP was tested for its ability to bind to GST-E6 proteins (FIG. 6). Under the conditions tested, the 95 kd protein did not bind detectably to either GST (with no fusion; lane 1), or GST fusions to HPV 6 or 11 E6 (lanes 4 and 5). Binding was seen with both the GST-16 E6 and 18 E6 fusion proteins (lanes 2 and 3). Binding to the HPV16 E6 fusion protein was reproducibly greater than to the HPV18 E6 fusion protein. Similar results obtained with the 76 kd form of the translated ORF. Since HPV16 E6 associates with p53 with a higher apparent affinity than HPV18 E6 (Werness el al., supra, 1990), this suggests that the affinity of an HPV E6 protein for p53 may be directly related to its affinity for E6-AP.

Example 4

This example demonstrates that E6 mediated degradation of p53 is dependent upon the presence of E6-AP. High risk HPV E6 proteins target p53 for ubiquitination and proteolytic degradation when both are synthesized in rabbit reticulocyte lysate (Scheffner et al., *Cell*, 63:1129–1136 (1990)). The components of the ubiquitin proteolysis system are present in rabbit reticulocyte lysate and in wheat germ extract (Hatfield and Vierstra, *Biochem.*, 28:735–742 (1989)), yet p53 is stable in the presence of HPV16 E6 when both are synthesized in wheat germ extract as described below.

Unlike rabbit reticulocyte lysate, wheat germ extract does not contain E6-AP activity and therefore association between E6 and p53 is not detected. The addition of a highly purified E6-AP fraction to wheat germ extract-translated p53 resulted in the ubiquitination of p53 in the presence of HFV16 E6, however it could not be ruled out that even this highly purified E6-AP fraction might contain additional factors that might be required for E6-mediated ubiquitination. To determine if E6-AP is the only additional component necessary to stimulate E6-mediated degradation in wheat germ extract, the 95 and 76 kd E6-AP proteins were tested for their ability to stimulate the E6-mediated degradation of p53 when all three components were translated in wheat germ extract. As shown in FIG. 7, p53 was stable in the presence of HPV16 E6 alone or either the 95 or 76 kd forms of E6-AP alone. The addition of both HPV16 E6 and either the 95 or 76 kd forms of E6-AP resulted in the degradation of p53. The 76 kd protein was slightly more active in promoting p53 degradation than the 95 kD protein, possibly because the 76 kd protein was present in a higher amount since it is translated more efficiently. This shows that E6-AP is the only component missing in wheat germ extract that is necessary for E6-mediated degradation of p53, and that the N-terminal 212 amino acids encoded by the cloned ORF are not required for E6-mediated p53 degradation in vitro.

Example 5

This example demonstrates identification of the E6 binding domain of E6-AP. Glutathione S-transferase-E6-AP peptide fragment fusion proteins were constructed and tested for the ability to bind E6-AP. The binding domain was shown to be localized within a 70 amino acid region, between amino acids 371 and 440 of SEQ ID NO:1.

Plasmids for the expression of E6-AP fusion proteins were constructed. Nucleic acid sequences encoding polypeptide fragments of E6-AP were amplified by polymerase chain reaction (PCR). The amplification products were ligated into pGEX-2T plasmids (Pharmacia) for expression of GST fusion proteins in *E. coli;* into pGEM1 (Promega) for in vitro transcription and translation; and into pVL1393 (Pharmingen) for expression in insect cells. Sense oligonucleotides containing a Kozak consensus translation initiation codon (except pGEX-2T) were synthesized, and antisense oligonucleotides containing an in-frame translation stop codon were synthesized.

The pGEX-2T-E6-E7 plasmid was constructed by ligation of HPV16 E6 and HPV16 E7 open reading frames into pGEX-2TK as described in Kaelin, *Cell,* 70:351–364 (1992), incorporated herein by reference. The protein expressed by this plasmid in *E. coli* was a GST followed by a protein kinase A site followed by the E6 and E7 sequences. A 2-amino acid segment (Val-Asp) was encoded by the SalI restriction site linking the E6 and E7 sequences. Following purification, the protein was labeled in vitro with [$\gamma$-$^{32}$P]ATP (Amersham) and protein kinase A (Sigma).

GST fusion proteins were expressed in *E. coli* DH5α and affinity purified on glutathione-Sepharose (Pharmacia). Rabbit reticulocyte and wheat germ in vitro translation reagents were obtained from Promega. Recombinant baculoviruses were recovered by using the BaculoGold transfection kit (Pharmingen) as described by the manufacturer.

E6 binding assays were performed by combining approximately 0.1 µg of GST or GST-E6-AP fusion protein immobilized on glutathione-Sepharose with 125 µl of $T_{25}N_{50}$ (25 mM Tris-HCl (pH 7.4)50 mM NaCl), 25 µl of lysis buffer (100 mM Tris-HCl (pH 7.4), 100 mM NaCl, 1% Nonidet P-40), and 10 µl of a $^{35}$S-labeled HPV16 E6 wheat germ extract translation reaction mixture. The mistures were rotated in microcentrifuge tubes at 4° C. for 12 hours. The Sepharose beads were colected by centrifugation, washed three times with 750 µl of lysis buffer, and boiled for 5 minutes in sodium dodecyl sulfate (SDS) gel loading buffer. The amount of $^{35}$S-labeled E6 protein that bound to the beads was determined by SDS-polyacrylamide gel electrophoresis (PAGE; 12% acrylamide) and fluorography. A total of 1 µl of the translation reaction mixture was run on the gel to determine the fraction of the input E6 protein that bound to the GST-E6-AP proteins. Peptide competition binding assays were performed as described above in the presence of peptides corresponding to amino acids 391–408 or 640–653 of SEQ ID NO:1 (E6-AP).

Figure 8A:
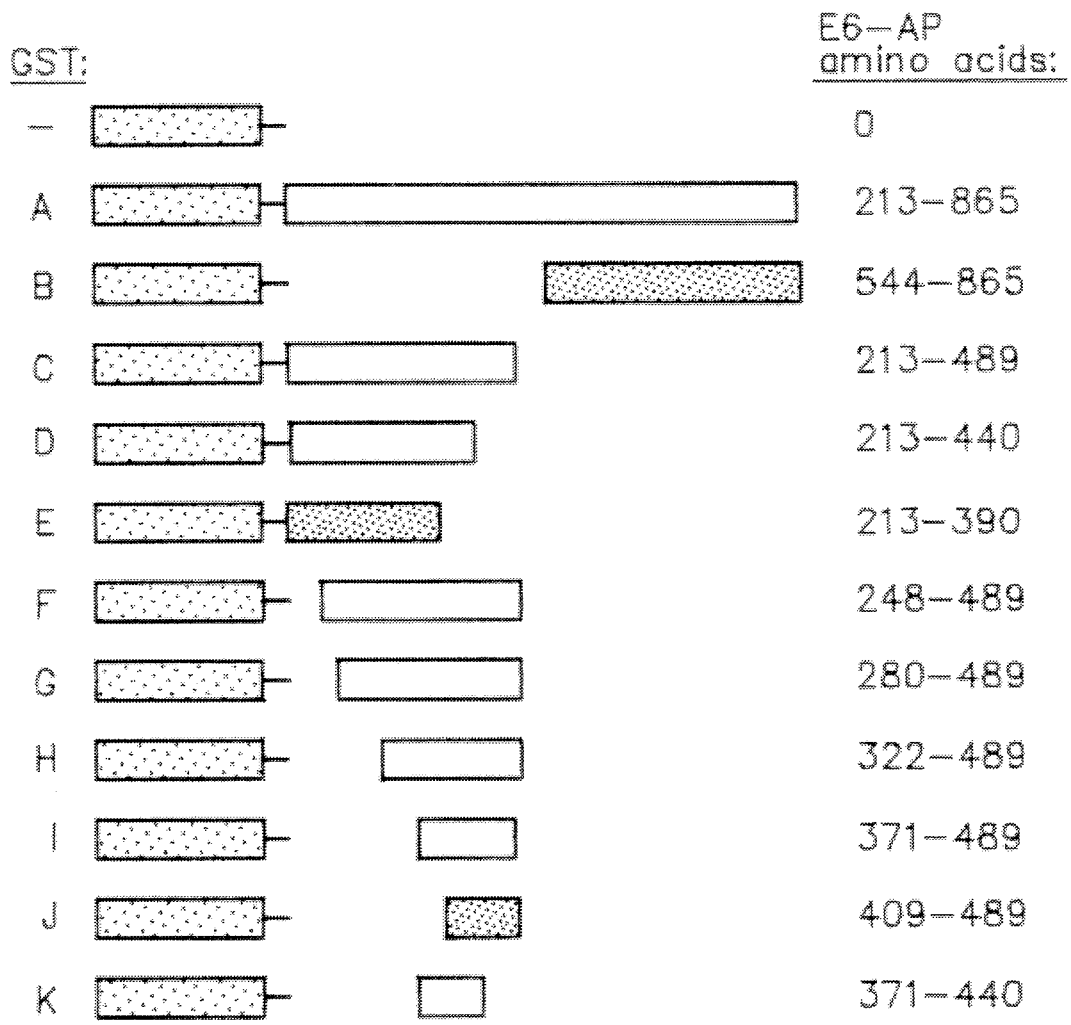
FIGS. 8A and 8B illustrate binding of fragments of SEQ ID NO:1 with HPV16 E6.
Figure 8B:

E6-AP can stably associate with high risk HPV E6 proteins in the absence of p53. The largest segment of E6-AP fused to GST consisted of the C-terminal 653 amino acids (amino acids 212–865 of SEQ ID NO:1). This 75 kDa fragment of E6-AP contains all of the sequences necessary to direct association of E6 with p53 and induce degradation of p53 by ubiquitination. Equal amounts (approximately 0.1 µg) of different GST-E6-AP fragment fusion proteins were assayed for the ability to associate with HPV16 or HPV11 E6 proteins by mixing the GST fusion proteins, immobilized on glutathione-Sepharose, with in vitro-translated $^{35}$S-labeled E6 proteins. Wheat germ extract was used for translation of E6 proteins. The level of binding considered non-specific was that amount of E6 protein that bound to GST lacking E6-AP protein sequences. FIG. 8A illustrates a schematic representation of the regions of E6-AP assayed for E6 association. FIG. 8B illustrates binding of the fusion proteins to labeled E6. The 75 kDa form of the E6-AP and the amino-terminal portion (amino acids 213 to 489 of SEQ ID NO:1) of the this region bound specifically to HPV16 E6. The carboxy-terminal portion of E6-AP (amino acids 544 to 865 of SEQ ID NO:1) did not bind to HPV16 E6. Binding assays of additional fusion proteins containing amino acid sequences of the amino-terminal region demonstrated that the E6 binding domain is between amino acids 371 and 440 of SEQ ID NO:1 (also referred to as SEQ ID NO:2). This E6-AP fragment is encoded by SEQ ID NO:5. These fusion proteins bound approximately 50% of the input $^{35}$S-labeled HPV16 E6. None of the E6-AP fusion proteins bound HPV11 E6 above the background level.

Figure 9A:
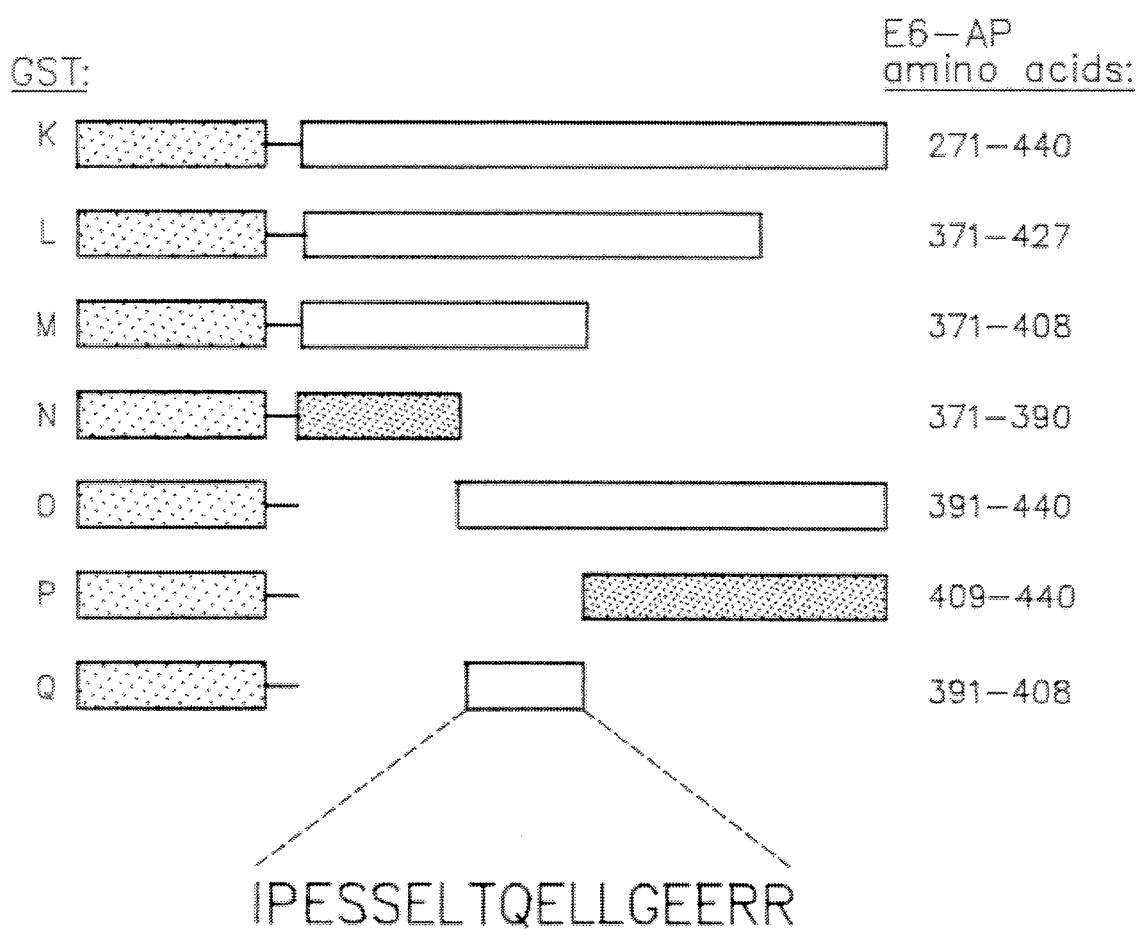
FIGS. 9A and 9B illustrate an polypeptide variants of SEQ ID NO:2 and their binding to HPV16 E6.
Figure 9B:

Fusion proteins containing regions of E6-AP between amino acids 371 and 440 of SEQ ID NO:1 were synthesized as described above. These fusion proteins were assayed for binding to HPV E6. The results are demonstrated in FIGS. 9A and 9B. These assays localized the binding region to an 18 amino acid region from amino acid 391 to 408 of SEQ ID NO:1 (also referred to as SEQ ID NO:3). This 18 mer polypeptide is encoded by SEQ ID NO:6. A GST fusion protein was constructed that included the 75 kDa fragment with this 18 mer segment deleted. This fusion protein did not bind HPV16 E6. A synthetic peptide consisting of only this 18 mer region competed for binding of HPV16 E6 with the GST-75 kDa E6-AP fusion protein. Fifty percent binding competition was acheived with approximately a 5000 fold molar excess over the GST-E6-AP fusion protein. This demonstrates that the 18 mer peptide (SEQ ID NO:3) are necessary and sufficient for stable association with HPV16 E6.

Example 6

This example demonstrates determination of p53 binding domains in E6-AP. Assayed proteins were synthesized as described above. Deletion mutants indicate that amino acids in the region from amino acid 280–781 of SEQ ID NO:1 were necessary for stable association of p53 with HPV16 E6.

The p53 binding assays were performed by mixing 0.1 µg of GST-p53 protein (synthesized as described in Huibregtse, *EMBO J.*, 13:4129–4135 (1991), incorporated herein by reference) immobilized on glutathione-Sepharose with $T_{25}N_{50}$, 25 ml of the lysis buffer described in Example 5, 10 µl of a rabbit reticulocyte lysate in vitro translation reaction mixture containing $^{35}$S-labeled E6-AP protein, and 10 µl of either a mock wheat germ extract translation reaction mixture or an HPV16 E6 RNA-programmed wheat germ extract translation reaction mixture. The mixtures were incubated and processed as described in Example 5 for E6 binding reactions. Aliquots of the E6-AP translation reaction mixtures were analyzed separately by SDS-PAGE to ensure that all E6-AP variants were translated with similar efficiencies.

Neither E6 nor E6-AP alone stably associate with p53. Several amino- and carboxy-terminal deletion mutants of E6-AP were constructed in an in vitro transcription and translation vector as demonstrated in FIG. 10A. The largest E6-AP cDNA encoded amino acids 37 to 865 of SEQ ID NO:1. The protein encoded has all of the p53 and E6 binding attributes of E6-AP protein purified from human cells. In addition to the N- and C-terminal deletions, an internal deletion of the 18 amino acid E6 binding domain was constructed. The E6-AP variants were synthesized in rabbit reticulocyte lysate as $^{35}$S-labeled proteins.

Equivalent amounts of these proteins were mixed with glutathione-Sepharose beads containing GST-p53 fusion protein (wild-type p53). FIGS. 10B and 10C demonstrate p53 binding of the deletion mutant fusion proteins with p53. Deletion of N-terminal sequences to amino acids 213, 248, and 280 had less than a fourfold effect on the ability E6-AP to associate with wild-type p53. Further deletion of N-terminal sequences to amino acid 322 or beyond led to nearly complete loss of binding. C-terminal truncation to amino acid 831 or 781 resulted in slight p53 binding reduction. Further C-terminal truncation abolished binding. p53 binding variations in the E6-AP mutants indicate that sequences flanking the 502 amino acid sequence between amino acids 280 and 781 influence p53 binding activity. FIG. 10D demonstrates that deletion of the 18 mer segment (amino acids 391–408) abolished p53 binding activity.

Example 7

This example demonstrates localization of E6-AP sequences necessary for p53 ubiquitination.

p53 ubiquitination assays were performed by combining 2 µl of $^{35}$S-labeled wheat germ extract-translated human wild-type p53 with 10 µl of either a mock wheat germ extract translation reaction mixture or a wheat germ extract translation mixture programmed with HPV16 E6 mRNA and with 10 µl of the DEAE fraction from either uninfected S19 cells or baculovirus-infected S19 cells. Additionally, each reaction mixture contained 24 µl of $T_{25}N_{50}$, 2 µl of 2 mg/ml ubiquitin (Sigma), and 2 µl of 40 mM ATP-γ-S (total volume, 50 µl). The mixtures were incubated at room temperature for 4 hours and then analyzed by SDS-PAGE and fluorography.

Ubiquitination assays with $^{32}$P-labeled GST-E6-E7 as the substrate were performed by combining 0.02 µg of the labeled protein, 2 µl of 2 mg/ml ubiquitin, 2 µl of 40 mM ATP-γ-S, 2 µl of 100 mM dithiothreitol, 0.5 µl of 0.15M MgCl$_2$, 10 μl of a DEAE fraction, and T$_{25}$N$_{50}$ to a final volume of 50 μl. The mixtures were incubated at room temperature for 4 hours and then analyzed by SDS-PAGE and autoradiography.

Figure 11A:
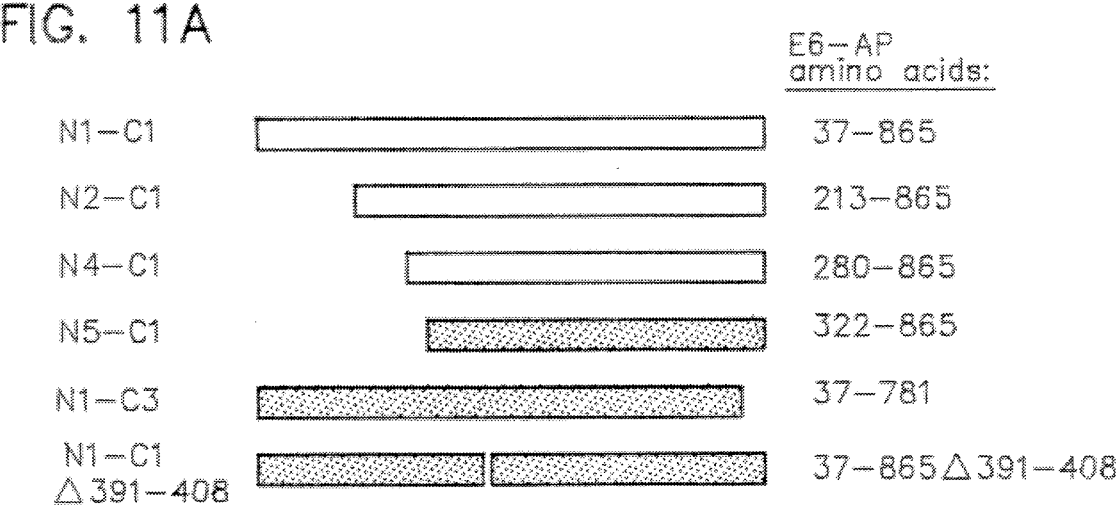
FIGS. 11A–C illustrate p53 ubiquitination in the presence of E6 and variant E6-Ap proteins.

To assay E6-AP proteins for their abilities to stimulate the degradation of p53, several E6-AP variants were expressed in S19 insect cells by using a baculovirus expression system. S19 cells lack endogenous E6-AP activity. The E6-AP variants that were expressed are shown schematically in FIG. 11A. E6-AP proteins from baculovirus-infected S19 cell extracts were partially purified in a single-batch chromatography step with DEAE-Sephacell. When the high salt eluates were run on an SDS-polyacrylamide gel and stained with Coomassie blue, a band corresponding to the appropriate molecular weight of each of the E6-AP variants was clearly visible by comparison to the protein fraction obtained from either uninfected S19 cells or S19 cells infected with wild-type virus that did not express a foreign protein. The amounts of DEAE fractions were adjusted according to the stained gel so that approximately equal levels of E6-AP proteins were used in each assay.

Figure 11B:
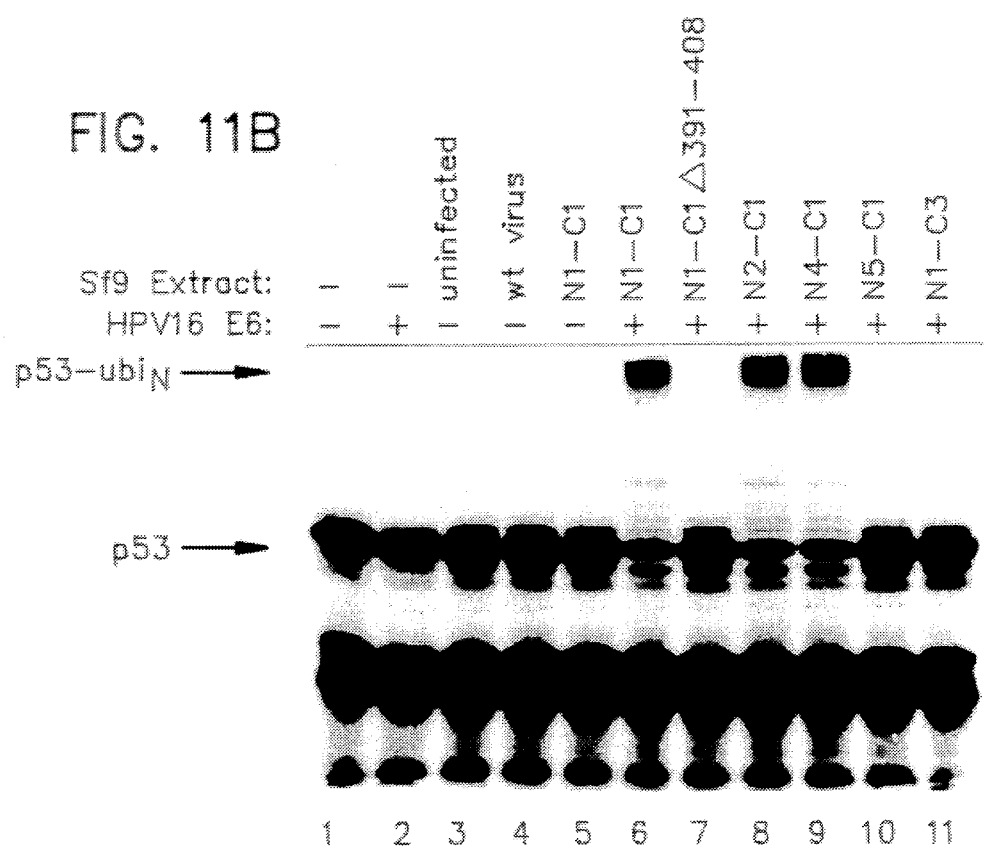
Figure 11C:
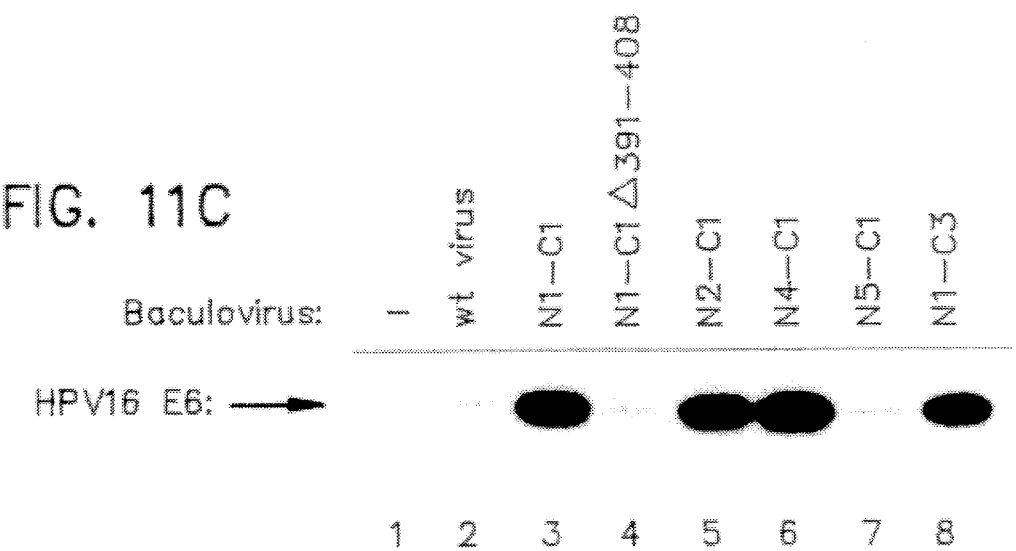

Use of ATP-γ-S ATP analogs allows ubiquitination of subtrates while inhibiting subsequent proteolytic degradation. This results in accumulation of high-molecular-weight multiubiquitinated products. As shown in FIG. 11B, p53 was not ubiquitinated in the presence of only HPV16 E6 or in the presence of only a DEAE fraction from uninfected S19 cells, from S19 cells infected with wild-type baculovirus, or from cells infected with virus expressing the Ni-Cl form of E6-AP (lanes 2–5, respectively). HPV16 E6 combined with the DEAE fraction containing the N1-C1 form of E6-AP led to accumulation of high-molecular-weight forms of p53 with a corresponding decrease in the amount of nonubiquitinated p53 (lane 6). The DEAE fraction containing the E6-AP fraction lacking the 18-amino acid E6 binding sequence (N1-C1Δ391–408) did not stimulate the ubiquitination of p53 (lane 7). The DEAE fractions containing the N-terminally truncated forms of E6-AP beginning at amino acids 213 or 280 (N2-C1 and N4-C1) stimulated the ubiquitination of p53 in the presence of HPV16 E6, while the N-terminally truncated E6-AP beginning at amino acid 322 (N5-C1) did not (lanes 8–11). This corresponds with the ability of the variants to associate with p53. Because the C-terminally truncated form of E6-AP was unable to stimulate ubiquitination of p53, the C-terminal 84 amino acids are necessary for E6-induced ubiquitination, but not for binding to p53. This variant form was shown to form a stable complex with E6 and p53. In fact, DEAE fractions containing the N1-C1, N2-C1, N4-C1, and N1-C3 forms could stimulate association of HPV16 E6 with p53 (FIG. 11C). Neither the E6-AP variant lacking the E6 binding domain (N1-C1Δ391–408) nor the N-terminally truncated form beginning at amino acid 322 (N5-C1) could stimulate the association.

E6-AP sequences required for ubiquitination of an artificial E6 fusion protein were localized. This was assessed by identifying ubiquitination of a GST-HPV16 E6-HPV16 E7 fusion protein. This protein is unstable in the presence of E6-AP and stimulates its own ubiquitination. As p53 is not needed to stimulate ubiquitination, the large region needed for p53 binding could be further dissected to identify necessary regions for ubiquitination.

Figure 12:
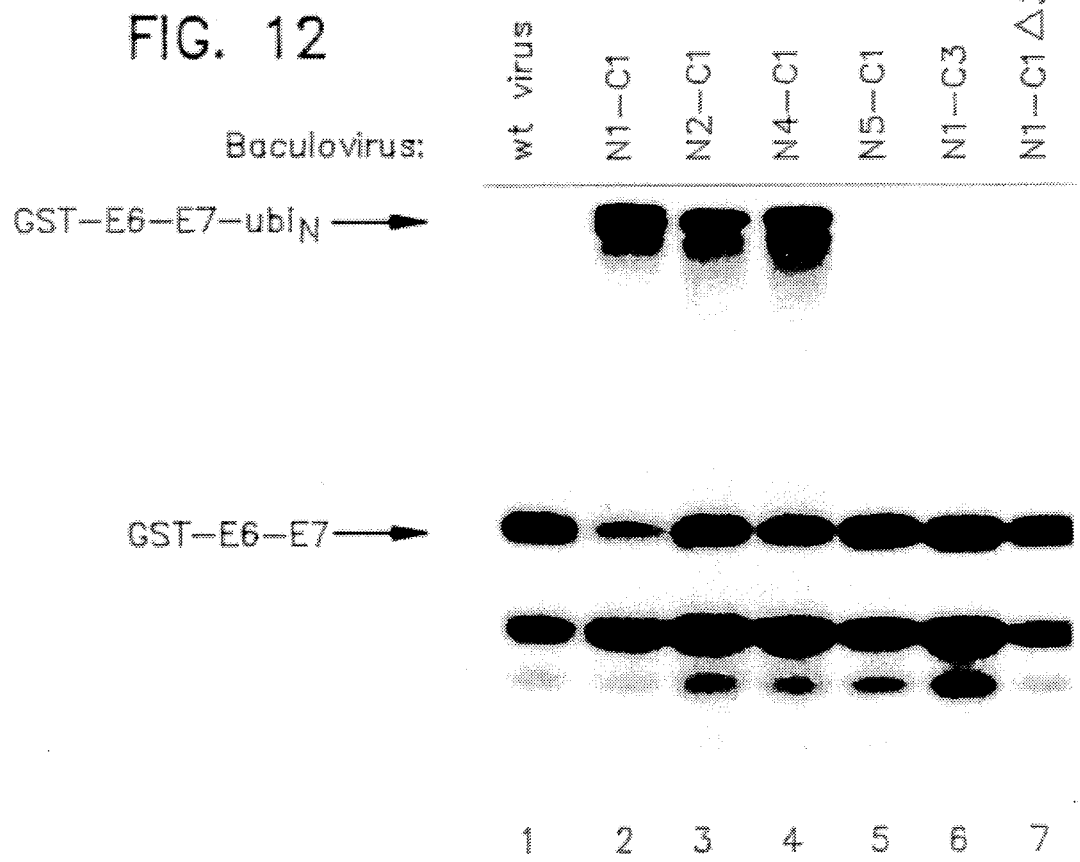
FIG. 12 illustrates an assay for ubiquitination of GST-E6-E7 fusion protein.

The fusion protein was expressed in *E. coli* and contains a protein kinase A site between the GST sequence and the E6 sequence that allowed labeling with $^{32}$p following purification as described in Kaclin et al., *Cell, 70:351–364* (1992). Labeled GST-E6-E7 protein was mixed with unprogrammed wheat germ extract containing the general components of the ubiquitin proteolysis system and DEAE fractions from baculovirus-infected S19 cells as described above. The addition of wheat germ extract alone had no effect on the stability or ubiquitination of the fusion protein, nor did the addition of wheat germ extract plus DEAE fractions from uninfected S19 cells or S19 cells infected with wild-type virus (FIG. 12). DEAE fractions containing the 95-kDa E6-AP (N1-C1) and the N-terminally truncated E6-AP variants beginning at amino acid 213 or 280 (N2-C1 and N4-C1, respectively) stimulate ubiquitination of the fusion protein. The internally deleted E6-AP lacking the E6 binding site (N1-C 1Δ391–408), the N-terminally truncated E6-AP beginning at amino acid 322 (N5-C1), and the C-terminally truncated E6-AP lacking the last 84 amino acids (N1-C3) did not stimulate ubiquitination of the fusion protein. This demonstrates that the 84 C-terminal amino acids as well as sequences between amino acids 280 and 322 are important for E6-AP-dependent ubiquitination. Therefore, the minimal region of E6-AP required for ubiquitination of associated proteins spans a region that begins about 90 amino acids N-terminal to the E6 binding domain and extends to a region encompassing the last 84 amino acids. The E6 binding domain, the minimal region that can direct association with p53, and the minimal region required for ubiquitination of p53 and the E6–E7 fusion protein are illustrated in FIG. 13.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be apparent that certain changes and modifications may be practiced within the scope of the appended claims.

---

What is claimed is:

1. A DNA construct encoding E6 Associated Protein which comprises the following operably linked elements:
    a transcriptional promoter;
    a DNA sequence encoding E6 Associated Protein; and
    a transcriptional terminator;
    wherein said E6 Associated Protein is a polypeptide which comprises an amino acid subsequence of at least six contiguous amino acids of SEQ ID NO:3 and has at least one of the following properties: (1) stably associates with wild-type p53 in the presence of HPV16 E6, (2) stimulates the association of HPV16 E6 with p53, and (3) stably associates with a high risk HPV E6 protein in the absence of p53.

2. A DNA construct as in claim 1, wherein the E6 Associated Protein is of human origin.

3. A DNA construct as in claim 2, wherein the DNA sequence encoding E6 Associated Protein is homologous to SEQ ID NO:4.

4. A DNA construct as in claim 2, wherein the E6 Associated Protein is homologous to SEQ ID NO:5.

5. A DNA construct as in claim 2, wherein the E6 Associated Protein is homologous to SEQ ID NO:6.

\* \* \* \* \*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 866 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

| Ser | Gly | Glu | Pro | Gln | Ser | Asp | Asp | Ile | Glu | Ala | Ser | Arg | Met | Lys | Arg |
|---|---|---|---|---|---|---|---|---|---|---|---|---|---|---|---|
| 1 | | | | 5 | | | | | 10 | | | | | 15 | |

| Ala | Ala | Ala | Lys | His | Leu | Ile | Glu | Arg | Tyr | Tyr | His | Gln | Leu | Thr | Glu |
| | | | 20 | | | | | 25 | | | | | 30 | | |

| Gly | Cys | Gly | Asn | Glu | Ala | Cys | Thr | Asn | Glu | Phe | Cys | Ala | Ser | Cys | Pro |
| | | 35 | | | | 40 | | | | | 45 | | | | |

| Thr | Phe | Leu | Arg | Met | Asp | Asn | Lys | Ala | Ala | Ala | Ile | Lys | Ala | Leu | Glu |
| | 50 | | | | | 55 | | | | | 60 | | | | |

| Leu | Tyr | Lys | Ile | Asn | Ala | Lys | Leu | Cys | Asp | Pro | His | Pro | Ser | Lys | Lys |
| 65 | | | | | 70 | | | | 75 | | | | | | 80 |

| Gly | Ala | Ser | Ser | Ala | Tyr | Leu | Glu | Asn | Ser | Lys | Gly | Ala | Pro | Asn | Asn |
| | | | | 85 | | | | | 90 | | | | | 95 | |

| Ser | Cys | Ser | Glu | Ile | Lys | Met | Asn | Lys | Lys | Gly | Ala | Arg | Ile | Asp | Phe |
| | | | 100 | | | | | 105 | | | | | 110 | | |

| Lys | Asp | Val | Thr | Tyr | Leu | Thr | Glu | Glu | Lys | Val | Tyr | Glu | Ile | Leu | Glu |
| | | 115 | | | | | 120 | | | | | 125 | | | |

| Leu | Cys | Arg | Glu | Arg | Glu | Asp | Tyr | Ser | Pro | Leu | Ile | Arg | Val | Ile | Gly |
| | 130 | | | | | 135 | | | | | 140 | | | | |

| Arg | Val | Phe | Ser | Ser | Ala | Glu | Ala | Leu | Val | Gln | Ser | Phe | Arg | Lys | Val |
| 145 | | | | | 150 | | | | | 155 | | | | | 160 |

| Lys | Gln | His | Thr | Lys | Glu | Glu | Leu | Lys | Ser | Leu | Gln | Ala | Lys | Asp | Glu |
| | | | | 165 | | | | | 170 | | | | | 175 | |

| Asp | Lys | Asp | Glu | Asp | Glu | Lys | Glu | Lys | Ala | Ala | Cys | Ser | Ala | Ala | Ala |
| | | | 180 | | | | | 185 | | | | | 190 | | |

| Met | Glu | Glu | Asp | Ser | Glu | Glu | Ala | Ser | Ser | Ser | Arg | Ile | Gly | Asp | Ser |
| | | 195 | | | | | 200 | | | | | 205 | | | |

| Ser | Gln | Gly | Asp | Asn | Asn | Leu | Gln | Lys | Leu | Gly | Pro | Asp | Asp | Val | Ser |
| | 210 | | | | | 215 | | | | | 220 | | | | |

| Val | Asp | Ile | Asp | Ala | Ile | Arg | Arg | Val | Tyr | Thr | Arg | Leu | Leu | Ser | Asn |
| 225 | | | | | 230 | | | | | 235 | | | | | 240 |

| Glu | Lys | Ile | Glu | Thr | Ala | Phe | Leu | Asn | Ala | Leu | Val | Tyr | Leu | Ser | Pro |
| | | | | 245 | | | | | 250 | | | | | 255 | |

| Asn | Val | Glu | Cys | Asp | Leu | Thr | Tyr | His | Asn | Val | Tyr | Ser | Arg | Asp | Pro |
| | | | 260 | | | | | 265 | | | | | 270 | | |

| Asn | Tyr | Leu | Asn | Leu | Phe | Ile | Ile | Gly | Met | Glu | Asn | Arg | Asn | Leu | His |
| | | 275 | | | | | 280 | | | | | 285 | | | |

| Ser | Pro | Glu | Tyr | Leu | Glu | Met | Ala | Leu | Pro | Leu | Phe | Cys | Lys | Ala | Met |
| | 290 | | | | | 295 | | | | | 300 | | | | |

| Ser | Lys | Leu | Pro | Leu | Ala | Ala | Gln | Gly | Lys | Leu | Ile | Arg | Leu | Trp | Ser |
| 305 | | | | | 310 | | | | | 315 | | | | | 320 |

| Lys | Tyr | Asn | Ala | Asp | Gln | Ile | Arg | Arg | Met | Met | Glu | Thr | Phe | Gln | Gln |
| | | | | 325 | | | | | 330 | | | | | 335 | |

| Leu | Ile | Thr | Tyr | Lys | Val | Ile | Ser | Asn | Glu | Phe | Asn | Ser | Arg | Asn | Leu |
| | | | 340 | | | | | 345 | | | | | 350 | | |

| Val | Asn | Asp | Asp | Asp | Ala | Ile | Val | Ala | Ala | Ser | Lys | Cys | Leu | Lys | Met |
| | | 355 | | | | | 360 | | | | | 365 | | | |

| Val | Tyr | Tyr | Ala | Asn | Val | Val | Gly | Gly | Glu | Val | Asp | Thr | Asn | His | Asn |
| | 370 | | | | | 375 | | | | | 380 | | | | |

| Glu | Glu | Asp | Asp | Glu | Glu | Pro | Ile | Pro | Glu | Ser | Ser | Glu | Leu | Thr | Leu |
| 385 | | | | | 390 | | | | | 395 | | | | | 400 |

```
Gln  Glu  Leu  Leu  Gly  Glu  Glu  Arg  Arg  Asn  Lys  Lys  Gly  Leu  Arg  Val
               405                      410                      415

Asp  Pro  Leu  Glu  Thr  Glu  Leu  Gly  Val  Lys  Thr  Leu  Asp  Cys  Arg  Lys
               420                      425                      430

Pro  Leu  Ile  Pro  Phe  Glu  Glu  Phe  Ile  Asn  Glu  Pro  Leu  Asn  Glu  Val
               435                      440                      445

Leu  Glu  Met  Asp  Lys  Asp  Tyr  Thr  Phe  Phe  Lys  Val  Glu  Thr  Glu  Asn
     450                      455                      460

Lys  Phe  Ser  Phe  Met  Thr  Cys  Pro  Phe  Ile  Leu  Asn  Ala  Val  Thr  Lys
465                      470                      475                      480

Asn  Leu  Gly  Leu  Tyr  Tyr  Asp  Asn  Arg  Ile  Arg  Met  Tyr  Ser  Glu  Arg
               485                      490                      495

Arg  Ile  Thr  Val  Leu  Thr  Ser  Leu  Val  Gln  Gly  Gln  Gln  Leu  Asn  Pro
               500                      505                      510

Tyr  Leu  Arg  Leu  Lys  Val  Arg  Arg  Lys  His  Ile  Ile  Asp  Asp  Ala  Leu
               515                      520                      525

Val  Arg  Leu  Glu  Met  Ile  Ala  Met  Glu  Asn  Pro  Ala  Asp  Leu  Lys  Lys
     530                      535                      540

Gln  Leu  Tyr  Val  Glu  Phe  Glu  Gly  Glu  Gln  Gly  Val  Asp  Glu  Gly  Gly
545                      550                      555                      560

Val  Ser  Lys  Glu  Phe  Phe  Gln  Leu  Val  Val  Glu  Glu  Ile  Phe  Asn  Pro
               565                      570                      575

Asp  Ile  Gly  Met  Phe  Thr  Tyr  Asp  Glu  Ser  Thr  Lys  Leu  Phe  Trp  Phe
               580                      585                      590

Asn  Pro  Ser  Ser  Phe  Glu  Thr  Glu  Gly  Gln  Phe  Thr  Leu  Ile  Gly  Ile
               595                      600                      605

Val  Leu  Gly  Leu  Ala  Ile  Tyr  Asn  Asn  Cys  Ile  Leu  Asp  Val  His  Gly
     610                      615                      620

Pro  Met  Val  Val  Tyr  Arg  Lys  Leu  Met  Gly  Lys  Lys  Gly  Thr  Phe  Arg
625                      630                      635                      640

Asp  Leu  Gly  Asp  Ser  His  Pro  Val  Leu  Tyr  Gln  Ser  Leu  Lys  Asp  Leu
               645                      650                      655

Leu  Glu  Tyr  Val  Gly  Asn  Val  Glu  Asp  Asp  Met  Met  Ile  Thr  Phe  Gln
               660                      665                      670

Ile  Ser  Gln  Thr  Asn  Leu  Phe  Gln  Asn  Pro  Met  Met  Tyr  Asp  Leu  Lys
               675                      680                      685

Glu  Asn  Gly  Asp  Lys  Ile  Pro  Ile  Thr  Asn  Glu  Asn  Arg  Lys  Glu  Phe
     690                      695                      700

Val  Asn  Leu  Tyr  Ser  Asp  Tyr  Ile  Leu  Asn  Lys  Ser  Val  Glu  Lys  Gln
705                      710                      715                      720

Phe  Lys  Ala  Phe  Arg  Arg  Gly  Arg  His  Met  Val  Thr  Asn  Glu  Ser  Pro
               725                      730                      735

Leu  Lys  Tyr  Leu  Phe  Arg  Pro  Glu  Glu  Ile  Glu  Leu  Leu  Ile  Cys  Gly
               740                      745                      750

Ser  Arg  Asn  Leu  Asp  Phe  Gln  Ala  Leu  Glu  Glu  Thr  Thr  Glu  Tyr  Asp
               755                      760                      765

Gly  Gly  Tyr  Thr  Arg  Asp  Ser  Val  Leu  Ile  Arg  Glu  Phe  Trp  Glu  Ile
     770                      775                      780

Val  His  Ser  Phe  Thr  Asp  Glu  Gln  Lys  Arg  Leu  Phe  Leu  Gln  Phe  Thr
785                      790                      795                      800

Thr  Gly  Arg  Asp  Arg  Ala  Pro  Val  Gly  Gly  Leu  Gly  Lys  Leu  Lys  Met
               805                      810                      815

Ile  Ile  Ala  Lys  Asn  Gly  Pro  Asp  Thr  Glu  Arg  Leu  Pro  Thr  Ser  His
               820                      825                      830
```

```
         Thr   Cys   Phe   Asn   Val   Leu   Leu   Pro   Glu   Tyr   Ser   Ser   Lys   Glu   Lys
                     835                     840                           845

Leu   Lys   Glu   Arg   Leu   Leu   Lys   Ala   Ile   Thr   Tyr   Ala   Lys   Gly   Phe   Gly
                     850                           855                     860

Met   Leu
         865
```

( 2 ) INFORMATION FOR SEQ ID NO:2:

( i ) SEQUENCE CHARACTERISTICS:
        ( A ) LENGTH: 70 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
         Ala   Asn   Val   Val   Gly   Gly   Glu   Val   Asp   Thr   Asn   His   Asn   Glu   Glu   Asp
         1                       5                           10                          15

Asp   Glu   Glu   Pro   Ile   Pro   Glu   Ser   Ser   Glu   Leu   Thr   Leu   Gln   Glu   Leu
                           20                          25                          30

Leu   Gly   Glu   Glu   Arg   Arg   Asn   Lys   Lys   Gly   Leu   Arg   Val   Asp   Pro   Leu
                     35                          40                          45

Glu   Thr   Glu   Leu   Gly   Val   Lys   Thr   Leu   Asp   Cys   Arg   Lys   Pro   Leu   Ile
                     50                          55                          60

Pro   Phe   Glu   Glu   Phe   Ile
         65                      70
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
         Ile   Pro   Glu   Ser   Ser   Glu   Leu   Thr   Leu   Gln   Glu   Leu   Leu   Gly   Glu   Glu
         1                       5                           10                          15

Arg   Arg
```

( 2 ) INFORMATION FOR SEQ ID NO:4:

( i ) SEQUENCE CHARACTERISTICS:
        ( A ) LENGTH: 2598 base pairs
        ( B ) TYPE: nucleic acid
        ( C ) STRANDEDNESS: single
        ( D ) TOPOLOGY: linear ( i i ) MOLECULE TYPE: protein ( i x ) FEATURE:
        ( A ) NAME/KEY: CDS
        ( B ) LOCATION: 1010..1321

( x i ) SEQUENCE DESCRIPTION: SEQ ID NO:4:

```
TCAGGAGAAC   CTCAGTCTGA   CGACATTGAA   GCTAGCCGAA   TGAAGCGAGC   AGCTGCAAAG        60

CATCTAATAG   AACGCTACTA   CCACCAGTTA   ACTGAGGGCT   GTGGAAATGA   AGCCTGCACG       120

AATGAGTTTT   GTGCTTCCTG   TCCAACTTTT   CTTCGTATGG   ATAATAAAGC   AGCAGCTATT       180

AAAGCCCTCG   AGCTTTATAA   GATTAATGCA   AAACTCTGTG   ATCCTCATCC   CTCCAAGAAA       240
```

```
GGAGCAAGCT CAGCTTACCT TGAGAACTCG AAAGGTGCCC CCAACAACTC CTGCTCTGAG    300
ATAAAAATGA ACAAGAAAGG CGCTAGAATT GATTTTAAAG ATGTGACTTA CTTAACAGAA    360
GAGAAGGTAT ATGAAATTCT TGAATTATGT AGAGAAAGAG AGGATTATTC CCCTTTAATC    420
CGTGTTATTG GAAGAGTTTT TTCTAGTGCT GAGGCATTGG TACAGAGCTT CCGGAAAGTT    480
AAACAACACA CCAAGGAAGA ACTGAAATCT CTTCAAGCAA AAGATGAAGA CAAAGATGAA    540
GATGAAAAGG AAAAAGCTGC ATGTTCTGCT GCTGCTATGG AAGAAGACTC AGAAGCATCT    600
TCCTCAAGGA TAGGTGATAG CTCACAGGGA GACAACAATT GCAAAAATT  AGGCCCTGAT    660
GATGTGTCTG TGGATATTGA TGCCATTAGA AGGGTCTACA CCAGATTGCT CTCTAATGAA    720
AAAATTGAAA CTGCCTTTCT CAATGCACTT GTATATTTGT CACCTAACGT GGAATGTGAC    780
TTGACGTATC ACAATGTATA CTCTCGAGAT CCTAATTATC TGAATTTGTT CATTATCGGA    840
ATGGAGAATA GAAATCTCCA CAGTCCTGAA TATCTGGAAA TGGCTTTGCC ATTATTTTGC    900
AAAGCGATGA GCAAGCTACC CCTTGCAGCC CAAGGAAAAC TGATCAGACT GTGGTCTAAA    960
TACAATGCAG ACCAGATTCG GAGAATGATG GAGACATTTC AGCAACTTAT TACTTATAAA   1020
GTCATAAGCA ATGAATTTAA CAGTCGAAAT CTAGTGAATG ATGATGATGC CATTGTTGCT   1080
GCTTCGAAGT GCTTGAAAAT GGTTTACTAT GCAAATGTAG TGGGAGGGGA AGTGGACACA   1140
AATCACAATG AAGAAGATGA TGAAGAGCCC ATCCCTGAGT CCAGCGAGCT GACACTTCAG   1200
GAACTTTTGG GAGAAGAAAG AAGAAACAAG AAAGGTCTTC GAGTGGACCC CCTGGAAACT   1260
GAACTTGGTG TTAAAACCCT GGATTGTCGA AAACCACTTA TCCCTTTTGA AGAGTTTATT   1320
AATGAACCAC TGAATGAGGT TCTAGAAATG GATAAAGATT ATACTTTTTT CAAAGTAGAA   1380
ACAGAGAACA AATTCTCTTT TATGACATGT CCCTTTATAT GAATGCTGT  CACAAAGAAT   1440
TTGGGATTAT ATTATGACAA TAGAATTCGC ATGTACAGTG AACGAAGAAT CACTGTTCTC   1500
TACAGCTTAG TTCAAGGACA GCAGTTGAAT CCATATTTGA GACTCAAAGT TAGACGTGAC   1560
CATATCATAG ATGATGCACT TGTCCGGCTA GAGATGATCG CTATGGAAAA TCCTGCAGAC   1620
TTGAAGAAGC AGTTGTATGT GGAATTTGAA GGAGAACAAG GAGTTGATGA GGGAGGTGTT   1680
TCCAAAGAAT TTTTTCAGCT GGTTGTGGAG GAAATCTTCA ATCCAGATAT GGTATGTTC    1740
ACATACGATG AATCTACAAA ATTGTTTTGG TTTAATCCAT CTTCTTTTGA AACAGAGGGT   1800
CAGTTTACTC TGATTGGCAT AGTACTGGGT CTGGCTATTT ACAATAACTG TATACTGGAT   1860
GTACATTTTC CCATGGTTGT CTACAGGAAG CTAATGGGGA AAAAGGAAC  TTTTCGTGAC   1920
TTGGGAGACT CTCACCCAGT TCTATATCAG AGTTTAAAAG ATTTATTGGA GTATGTTGGG   1980
AATGTGGAAG ATGACATGAT GATCACTTTC CAGATATCAC AGACAAATCT TTTTGGTAAC   2040
CCAATGATGT ATGATCTAAA GGAAAATGGT GATAAAATTC CAATTACAAA TGAAAACAGG   2100
AAGGAATTTG TCAATCTTTA TTCTGACTAC ATTCTCAATA AATCAGTAGA AAAACAGTTC   2160
AAGGCTTTTC GGAGAGGTTT TCATATGGTG ACCAATGAAT CTCCCTTAAA GTACTTATTC   2220
AGACCAGAAG AAATTGAATT GCTTATATGT GGAAGCCGCA ATCTAGATTT CCAAGCACTA   2280
GAAGAAACTA CAGAATATGA CGGTGGCTAT ACCAGGGACT CTGTTCTGAT TAGGGAGTTC   2340
TGGGAAATCG TTCATTCATT TACAGATGAA CAGAAAAGAC TCTTCTTGCA GTTTACAACG   2400
GGCACAGACA GAGCACCTGT GGGAGGACTA GGAAAATTAA AGATGATTAT AGCCAAAAAT   2460
GGCCCAGACA CAGAAAGGTT ACCTACATCT CATACTTGCT TTAATGTGCT TTTACTTCCG   2520
GAATACTCAA GCAAAGAAAA ACTTAAAGAG AGATTGTTGA AGGCCATCAC GTATGCCAAA   2580
GGATTTGGCA TGCTGTAA                                                2598
```

( 2 ) INFORMATION FOR SEQ ID NO:5:

( i ) SEQUENCE CHARACTERISTICS:
        ( A ) LENGTH: 332 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
TCAGGAGAAC  CTCAGTCTGA  CGACATTGAA  GCTAGCCGAA  TGAAGCGAGC  AGCTGCAAAG        60
CATCTAATAG  AACGCTACTA  CCACCAGTTA  ACTGAGGGCT  GTGGAAATGA  AGCCTGCACG       120
TGCAAATGTA  GTGGGAGGGG  AAGTGGACAC  AAATCACAAT  GAAGAAGATG  ATGAAGAGCC       180
CATCCCTGAG  TCCAGCGAGC  TGACACTTCA  GGAACTTTTG  GGAGAAGAAA  GAAGAAACAA       240
GAAAGGTCTT  CGAGTGGACC  CCCTGGAAAC  TGAACTTGGT  GTTAAAACCC  TGGATTGTCG       300
AAAACCACTT  ATCCCTTTTG  AAGAGTTTAT  TA                                      332
```

( 2 ) INFORMATION FOR SEQ ID NO:6:

( i ) SEQUENCE CHARACTERISTICS:
        ( A ) LENGTH: 114 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
TCAGGAGAAC  CTCAGTCTGA  CGACATTGAA  GCTAGCCGAA  TGAAGCGAGC  AGCTGCAAAG        60
ATCCCTGAGT  CCAGCGAGCT  GACACTTCAG  GAACTTTTGG  GAGAAGAAAG  AAGA             114
```